US012653505B2

(12) United States Patent
Errico et al.

(10) Patent No.: US 12,653,505 B2
(45) Date of Patent: Jun. 16, 2026

(54) DEEP LEARNING-BASED REAL-TIME EYE-GAZE TRACKING FOR PORTABLE ULTRASOUND METHOD AND APPARATUS

(71) Applicant: KONINKLIJKE PHILIPS N.V., Eindhoven (NL)

(72) Inventors: Claudia Errico, Medford, MA (US); Grzegorz Andrzej Toporek, Cambridge, MA (US); Haibo Wang, Melrose, MA (US); Hua Xie, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 250 days.

(21) Appl. No.: 18/282,342

(22) PCT Filed: Mar. 16, 2022

(86) PCT No.: PCT/EP2022/056787
§ 371 (c)(1),
(2) Date: Sep. 15, 2023

(87) PCT Pub. No.: WO2022/200142
PCT Pub. Date: Sep. 29, 2022

(65) Prior Publication Data
US 2024/0164757 A1 May 23, 2024

Related U.S. Application Data

(60) Provisional application No. 63/163,970, filed on Mar. 22, 2021.

(51) Int. Cl.
*A61B 8/00* (2006.01)
*G06F 3/01* (2006.01)
*G02B 27/00* (2006.01)

(52) U.S. Cl.
CPC ............ *A61B 8/469* (2013.01); *A61B 8/4427* (2013.01); *A61B 8/463* (2013.01); *A61B 8/54* (2013.01); *G06F 3/013* (2013.01)

(58) Field of Classification Search
CPC ....... A61B 8/469; A61B 8/4427; A61B 8/463; A61B 8/54; G06F 3/013
See application file for complete search history.

(56) References Cited

U.S. PATENT DOCUMENTS

| | | | | |
|---|---|---|---|---|
| 2006/0109237 | A1* | 5/2006 | Morita | G16H 40/63 345/156 |
| 2011/0046483 | A1* | 2/2011 | Fuchs | A61B 18/1477 606/20 |

(Continued)

FOREIGN PATENT DOCUMENTS

| | | |
|---|---|---|
| CN | 102930170 A | 2/2013 |

OTHER PUBLICATIONS

International Search Report and Written Opinion for PCT/EP2022/056787; Mailing date: Jun. 24, 2022, 12 pages.
Zhang, D. et al., "Revealing Event Saliency in Unconstrained Video Collection", IEEE Trans. on Image Processing, 2017, vol. 26, No. 4, p. 1746-1758.
Wang, W. et al., "Deep cropping via attention box prediction and aesthetics assessment", IEEE International Conference on Computer Vision, 2017, 9 pages.

(Continued)

*Primary Examiner* — Colin T. Sakamoto

(57) ABSTRACT

An ultrasound portable system (10) and method comprise acquiring ultrasound images, via a smart device (14) and ultrasound probe (20), over a portion of an ultrasound scan protocol and/or ultrasound exam and presenting at least one acquired ultrasound image in an image space portion (24) of a display (16). Digital images are acquired, via a camera (18), of at least a device operator's head pose, and left and right eyes within respective digital images. Eye-gaze focus point locations on the smart device are determined within a combination of image space and control space (26) portions of the display via an image processing framework (36) configured to track the device operator's gaze and eye movement determined from the acquired digital images. The (Continued)

method further comprises performing a control function, selection of a control function, and/or a function to aid in a selection of a diagnostic measurement based on at least one determined eye-gaze focus point location of the determined eye-gaze focus point locations.

20 Claims, 11 Drawing Sheets

(56)                 References Cited

U.S. PATENT DOCUMENTS

| | | | |
|---|---|---|---|
| 2011/0130641 A1* | 6/2011 | Razzaque | A61B 8/5238 |
| | | | 600/407 |
| 2011/0137156 A1* | 6/2011 | Razzaque | A61B 34/20 |
| | | | 600/424 |
| 2013/0245428 A1* | 9/2013 | Banjanin | A61B 8/4263 |
| | | | 600/424 |
| 2015/0002490 A1* | 1/2015 | Han | A61B 8/462 |
| | | | 345/204 |
| 2015/0327841 A1* | 11/2015 | Banjanin | A61B 8/4263 |
| | | | 600/443 |
| 2016/0034031 A1* | 2/2016 | Kim | G06F 3/013 |
| | | | 345/629 |
| 2018/0042578 A1 | 2/2018 | Anand et al. | |
| 2019/0307419 A1* | 10/2019 | Durfee | A61B 8/14 |
| 2019/0340751 A1* | 11/2019 | Kim | G16H 50/20 |
| 2020/0126661 A1* | 4/2020 | Flexman | G16H 30/40 |
| 2020/0272229 A1* | 8/2020 | Sudarsky | G06T 19/20 |

OTHER PUBLICATIONS

Gao, D. et al., "Discriminant saliency for visual recognition from cluttered scenes", Advances in Neural Information Processing Systems, 2004, 9 pages.

Le Meur, O. et al., "A coherent computational approach to model bottom-up visual attention", IEEE Transactions on Pattern Analysis and Machine Intelligence, 2006, vol. 28, No. 5, pp. 802-817.

Gao, D. et al., "The discriminant center surround hypothesis for bottom-up saliency", Advances in Neural Information Processing Systems, 2008, pp. 497-504.

Gao, D. et al., "Discriminant saliency, the detection of suspicious coincidences, and applications to visual recognition", IEEE Transactions on Pattern Analysis and Machine Intelligence, 2009, vol. 31, No. 6, pp. 989-1005.

Krafka, K. et al., "Eye Tracking for Everyone", IEEE Conference on Computer Vision and Pattern Recognition (CVPR), 2016, pp. 2176-2184.

Andreoni, G. et al., "Motion analysis and eye tracking technologies applied to portable ultrasound systems user interfaces evaluation", 2013 International Conference on Computer Medical Applications (ICCMA), 2013, pp. 1-6.

Sharma, Y.C. et al., "SonoEyeNet: Standardized Fetal Ultrasound Plane Detection Informed by Eye Tracking", IEEE 15th International Symposium on Biomedical Imaging (ISBI 2018), 2018, pp. 1475-1478.

Hewener, H. et al., "Mobile ultrafast ultrasound imaging system based on smartphone and tablet devices," 2015 IEEE International Ultrasonics Symposium (IUS), 2015, pp. 1-4.

* cited by examiner

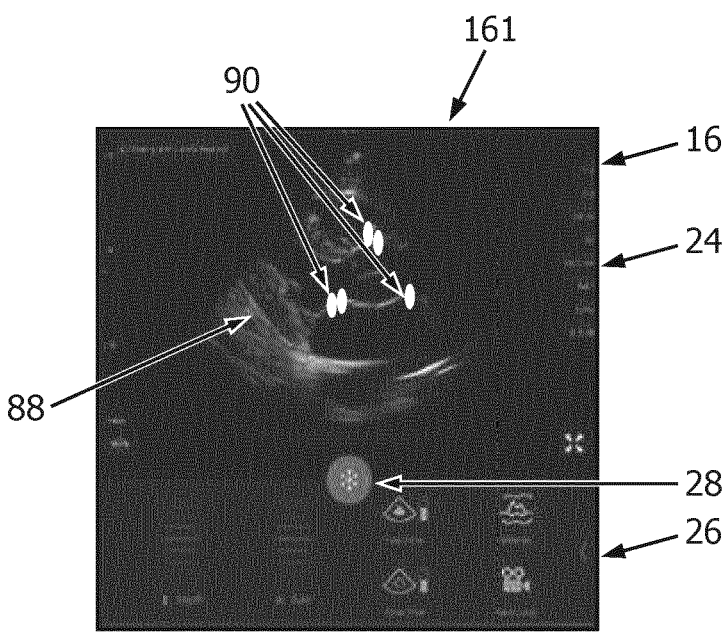
FIG. 6.1
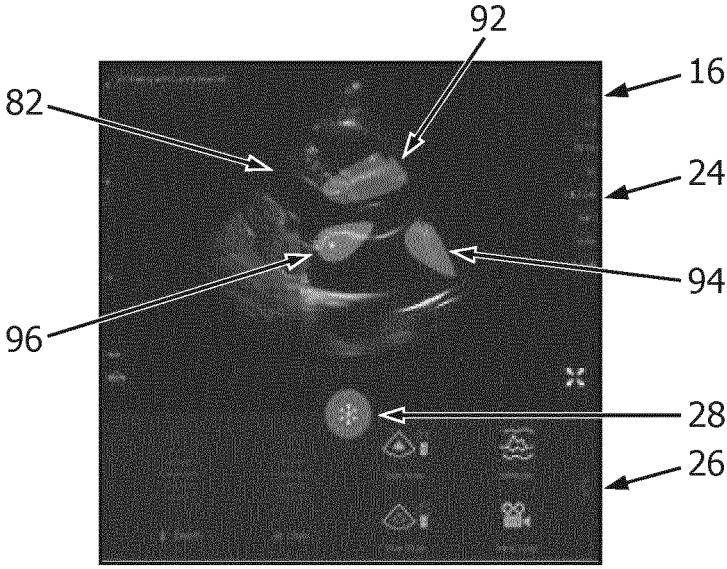
FIG. 6.2

DEEP LEARNING-BASED REAL-TIME EYE-GAZE TRACKING FOR PORTABLE ULTRASOUND METHOD AND APPARATUS

CROSS-REFERENCE TO PRIOR APPLICATIONS

This application is the U.S. National Phase application under 35 U.S.C. § 371 of International Application No. PCT/EP2022/056787, filed on Mar. 16, 2022, which claims the benefit of U.S. Provisional Patent Application No. 63/163,970, filed on Mar. 22, 2021. These applications are hereby incorporated by reference herein.

BACKGROUND

The present embodiments relate generally to portable ultrasound and more particularly, to a deep learning-based real-time eye-gaze tracking for portable ultrasound method and apparatus.

Ultrasound imaging is more accessible than ever thanks to technological advancement in high-quality portable devices. Ultra-mobile ultrasound imaging platforms such as Philips Lumify™, tablet ultrasound, or any ultrasound application on a smart phone, allow patients to be scanned, screened and diagnosed, whenever and wherever is needed. When portable handheld devices are used, there is generally a need for an immediate analysis and diagnosis. Philips Lumify™ handheld ultrasound portable devices provide operators and physicians with very high image quality to facilitate the decisions in point-of-care diagnoses, avoiding delays and/or need for the patient to travel.

The usage of mobile ultrasound may occur in various settings from bedside point-of-care inside an emergency department (ED), to critical settings outside of clinical infrastructures such as civilian emergency medicine, paramedic operations, and/or disaster relief. The compliance to scan protocols and the accuracy in interpretation of ultrasound images can vary significantly depending on user experience. Moreover, mobile ultrasound platforms are either hand-held by the user, or they need to be placed on a stand allowing operators to use their free hand to adjust the imaging settings and carry out measurements.

There exist several barriers to overcome in adopting the usage of mobile ultrasound devices. In a high percentage of the cases, the barriers break down into lack of training. Indeed, during patient scanning, users (i.e., device operators) should follow a standard protocol to capture or acquire all the information needed within the ultrasound images for a given ultrasound exam.

Usually, mobile ultrasound scanning protocols require device operators not only (i) to adjust acoustic settings (e.g., depth, gain, etc.) for image quality optimization depending on the body type under investigation, but also (ii) to transition from B-mode to other modes such as Color Doppler for functional imaging. In addition, very commonly for ultrasound, most image diagnostic measurements are performed off-line in a review mode and the acquisition of several B-mode loops (cine-loops) is necessary to further analyze the saved ultrasound images that have been acquired per the particular scanning protocol. Depending on a user's expertise level, the scanning protocol can be more or less straight forward for some users or device operators and the interpretation of the acquired ultrasound images can be more or less accurate.

Mobile ultrasound handheld platforms require either the user to hold the mobile ultrasound device in a free hand, opposite the probe-holding hand, or the mobile ultrasound device needs to be placed on a stand, or positioned on the patient to allow the sonographer to actually use his or her free hand to adjust imaging settings and/or to carry out any needed diagnostic ultrasound image measurements. With both hands in use, it can be clumsy and error-prone for a user to manipulate the controls needed for such adjustments or image measurement capture.

In addition, the usage of accessories to station (i.e., to place or to hold stationary) the smart phone or the tablet of an ultrasound mobile device during image acquisition or capture per a given scanning protocol is very limited. This is especially true with respect to ultrasound portable devices used in emergency settings where real-time capture and diagnosis is needed.

Various disadvantages with prior ultrasound methods and apparatus include workflow and user interaction challenges specific to mobile ultrasound. Accordingly, an improved method and apparatus for overcoming the problems in the art is desired.

SUMMARY

The inventors have realized various improvements to portable ultrasound systems which incorporate the tracking of the user's eye-gaze to supplement hand-operated controls and adjustments of the system. According to an embodiment of the present disclosure, a method is disclosed for real-time eye-gaze tracking for an ultrasound portable system. The ultrasound portable system comprises (i) a smart device having at least a display, (ii) a camera having a known spatial relationship relative to the display and (iii) an ultrasound probe coupled to the smart device, wherein the ultrasound portable system is for use by a device operator. The method comprises acquiring ultrasound images, via the smart device and the ultrasound probe, over a period of time. The period of time includes at least a portion of an ultrasound scan protocol and/or ultrasound exam. The method further comprises presenting, via at least the display, at least one ultrasound image of the acquired ultrasound images in an image space portion of the display. Digital images are acquired, via the camera over the period of time, wherein an image content within a field of view of the camera includes at least the device operator's head pose, and left and right eyes within respective digital images.

Eye-gaze focus point locations are determined or predicted on the smart device within at least (i) the image space portion, (ii) a control space portion, or (iii) a combination of the image space and control space portions of the display relative to the camera, via an image processing framework or a deep learning framework. The image processing framework or deep learning framework is configured to track gaze and eye movement and takes as input the device operator's gaze and eye movement determined from the acquired digital images. The method further comprises performing, via the smart device, one or more of a control function, a selection of a control function, and a function to aid in a selection of a diagnostic measurement according to the given ultrasound scan protocol and/or ultrasound exam, wherein the control function, selection of the control function, and/or the function to aid in the selection of the diagnostic measurement is based on at least one determined or predicted eye-gaze focus point location of the eye-gaze focus point locations. The selection of a control function may include selection of tissue presets or quantitative measurements.

In one embodiment, the image processing framework comprises a deep learning framework that includes at least one or more Convolutional Neural Networks (CNNs), long-short term memory (LSTM) networks and/or recurrent neural networks (RRN), and/or a cascade of the at least one or more Convolutional Neural Networks (CNNs), long-short term memory (LSTM) networks and/or recurrent neural networks (RRN).

In another embodiment, the method further comprises generating, via the smart device and with or without the deep learning framework, at least one attention map based on an accumulation of determined or predicted eye-gaze focus point locations for a given duration of time of an ultrasound acquisition, ultrasound scan protocol and/or ultrasound exam. In addition, the accumulation of determined or predicted eye-gaze focus point locations further defines a path that comprises a sequence of the determined or predicted eye-gaze focus point locations accumulated over time, wherein the path is identified with an action associated with a corresponding portion of the ultrasound scan protocol and/or ultrasound exam. Furthermore, in one embodiment, the path further comprises a sequence of the determined or predicted eye-gaze focus point locations accumulated over time corresponding to contour points in an ultrasound image having a desired sharpness of contours, and wherein the action comprises freezing the at least one ultrasound image being displayed in the image space portion of the display.

In yet another embodiment, the method further comprises comparing the at least one generated attention map to one or more command attention maps stored in memory. Each command attention map is based on a given track/path of the eyes for a given command of the ultrasound scan protocol and/or ultrasound exam. The method still further comprises executing, via the smart device, the given command, based on the comparison between the at least one generated attention map and the one or more command attention maps. In addition, the method further includes wherein the given command of a first command attention map of the one or more command attention maps comprises a command to automatically save the at least one ultrasound image being presented in the image space portion of the display.

In another embodiment, the method further includes wherein the given command of a second command attention map of the one or more command attention maps comprises one or more of (i) a command to automatically change an imaging modality of the ultrasound device from a first imaging modality to a second imaging modality, different from the first imaging modality, and (ii) a command to automatically select at least one ultrasound image from a cine-loop of multiple ultrasound images being displayed on the image space portion of the display. In yet another embodiment, the method further comprises outputting, via the smart device, at least one of a visual, audible, and/or tactile inquiry seeking confirmation for the smart device to execute the given command; and executing, via the smart device, the given command in response to receiving confirmation obtained via one or more determined or predicted eye-gaze focus point locations on the smart device within at least one of the image space portion or the control space portion of the display, via the deep learning framework. In one embodiment, the inquiry seeking confirmation comprises an overlay message on the display.

According to another embodiment, the method further comprises determining, via the smart device, an experience level of the device operator, wherein the experience level comprises an indicator of whether the device operator is an expert or a non-expert device operator, based on one or more determined or predicted eye-gaze focus point locations on the smart device within at least one of the image space portion or the control space portion of the display, via the deep learning framework; and performing at least the portion of the ultrasound scan protocol and/or ultrasound exam with assistance based on the determined experience level. The assistance can include (i) activating at least an inquiry seeking confirmation for the smart device to execute a given command in response to the determined experience level being a non-expert device operator, and (ii) de-activating the inquiry seeking confirmation in response the determined experience level being an expert device operator.

According to yet another embodiment, the camera comprises both a front-facing camera and a rear-facing camera, each having a respective fixed spatial relationship to the display, wherein the front-facing camera comprises the camera for acquiring digital images of the device operator. The method further comprises acquiring rear-facing digital images, via the rear-facing camera, over the period of time, of at least the ultrasound probe within a field of view of the rear-facing camera. A content of the rear-facing digital images includes at least a pose of the device operator's hand, or a pose of the ultrasound probe, within respective rear-facing digital images. The at least one rear-facing digital image of the acquired rear-facing digital images may be presented in the image space portion of the display.

Determining or predicting eye-gaze focus point locations on the smart device within at least one of the image space portion or the control space portion of the display further includes, via the deep learning framework, tracking gaze and eye movement with respect to the at least one rear-facing digital image being presented and taking as input the device operator's gaze and eye movement determined from the digital images acquired via the front-facing camera. The method further includes augmenting the image space portion, with or without presenting the at least one rear-facing digital image, with one or more augmented reality (AR) marker based on one or more determined or predicted eye-gaze focus point location on the smart device.

In still another embodiment, the method further comprises calibrating, via the smart device, a gaze tracking algorithm of the deep learning framework. The calibrating includes: starting the gaze tracking algorithm; receiving, via the display, a tapping input at a defined eye-gaze focus point location on the display chosen by the device operator; calculating an offset $(o_x, o_y)$ between (i) an estimated eye-gaze focus point location determined via the gaze tracking algorithm and (ii) the defined eye-gaze focus point location on the display; repeating the steps of receiving and calculating for a plurality of additional defined eye-gaze focus point locations and calculated offsets, until one or more system requirements are met; calculating an average offset $(\hat{o}_x, \hat{o}_y)$ between estimated and defined eye-gaze focus point locations; and using the average offset during subsequent use of the gaze tracking algorithm of the deep learning framework.

According to another embodiment, the method further comprises: inputting, via the smart device, an experience level of the device operator, wherein the experience level comprises a grading indicator of which category, or class, the device operator belongs in, wherein the categories or classes include at least resident (0), novice (1), and experienced user (2); and providing, via the smart device, an additional input to the deep learning framework for gaze prediction that describes the experience of the device operator for improving a prediction accuracy of the deep learning framework.

In one embodiment of the present disclosure, an ultrasound portable system with real-time eye-gaze tracking for use by a device operator, comprises a smart device having at least a display; a camera having a fixed spatial relationship to the display, wherein the camera is communicatively coupled to the smart device; and an ultrasound probe communicatively coupled to the smart device. The smart device is configured to: acquire ultrasound images, via the ultrasound probe over a period of time, wherein the period of time includes at least a portion of an ultrasound scan protocol and/or ultrasound exam; present, via at least the display, at least one ultrasound image of the acquired ultrasound images in an image space portion of the display; acquire digital images, via the camera over the period of time, wherein an image content within a field of view of the camera includes at least the device operator's head pose, and left and right eyes within respective digital images; and determine or predict eye-gaze focus point locations on the smart device within at least (i) the image space portion, (ii) a control space portion, or (iii) a combination of the image space and control space portions of the display relative to the camera, via an image processing framework or a deep learning framework.

The image processing framework or deep learning framework is configured to track gaze and eye movement and takes as input the device operator's gaze and eye movement determined from the acquired digital images. The smart device is further configured to perform one or more of a control function, a selection of a control function, and a function to aid in a selection of a diagnostic measurement according to the given ultrasound scan protocol and/or ultrasound exam, wherein the control function, the selection of the control function, and/or the function to aid in the diagnostic measurement is based on at least one determined or predicted eye-gaze focus point location of the eye-gaze focus point locations. The selection of a control function may include selection of tissue presets or quantitative measurements.

In a further embodiment, the system includes wherein the smart device is configured to generate, with or without the deep learning framework, at least one attention map based on an accumulation of determined or predicted eye-gaze focus point locations for a given duration of time of an ultrasound acquisition, ultrasound scan protocol and/or ultrasound exam. The at least one attention map can represent a mapping of areas on an ultrasound image that the device operator focuses upon during one or more portions of a scan protocol. An attention map could be generated based upon pre-planning of areas which a device operator should focus on during a scan protocol or portion thereof. In addition, a device operator's eye-gaze tracked focus point locations could also be tracked and/or predicted via a deep learning algorithm during an actual ultrasound exam or portion thereof. Furthermore, eye-gaze is not deep-learning based per se; however, in order to learn trends and correlations between attention maps and commands, the embodiments of the present disclosure use deep-learning for accurate predictions, i.e., to learn how to link together attention maps and commands to execute during an imaging exam. According to another embodiment, the smart device is further configured to: compare the at least one generated attention map to one or more command attention maps stored in memory, each command attention map being based on a given track/path of the eyes for a given command of the ultrasound scan protocol and/or ultrasound exam; and execute the given command, based on the comparison between the at least one generated attention map and the one or more command attention maps. In a further embodiment, the smart device is further configured to: output at least one of a visual, audible, and tactile inquiry seeking confirmation for the smart device to execute the given command; and execute the given command in response to receiving confirmation obtained via one or more determined or predicted eye-gaze focus point locations on the smart device within at least one of the image space portion or the control space portion of the display, via the deep learning framework.

In a still further embodiment, the system includes wherein the camera comprises both a front-facing camera and a rear-facing camera, each having a fixed spatial relationship to the display. The front-facing camera comprises the camera for acquiring digital images of the device operator. The smart device is further configured to: acquire rear-facing digital images, via the rear-facing camera, over the period of time, of at least the ultrasound probe within a field of view of the rear-facing camera. A content of the rear-facing digital images includes at least a pose of the device operator's hand, or a pose of the ultrasound probe, within respective rear-facing digital images.

The smart device is further configured to present, via at least the display, at least one rear-facing digital image of the acquired rear-facing digital images, wherein the at least one rear-facing digital image is presented in the image space portion of the display. In addition, the determined or predicted eye-gaze focus point locations on the smart device within at least one of the image space portion or the control space portion of the display further include determined or predicted eye-gaze focus point locations, via the deep learning framework. In addition, the deep learning framework is configured to track gaze and eye movement with respect to the at least one rear-facing digital image being presented and takes as input the device operator's gaze and eye movement determined from the digital images acquired via the front-facing camera. The smart device is still further configured to augment the image space portion, with or without presenting the at least one rear-facing digital image, with one or more augmented reality (AR) marker based on one or more determined or predicted eye-gaze focus point location on the smart device.

The embodiments of the present disclosure advantageously overcome the workflow and user interaction challenges specific to mobile ultrasound. The method and system of the present disclosure make use of a deep learning framework that takes as input operator's gaze and eye movement to assist the user to operate the ultrasound mobile device. For example, various workflow and user interaction challenges are overcome via one or more of user interface augmentation, commanding of the system, and operator performance evaluation, as discussed herein.

Still further advantages and benefits will become apparent to those of ordinary skill in the art upon reading and understanding the following detailed description.

BRIEF DESCRIPTION OF THE DRAWINGS

The embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements. In addition, it is to be noted that the figures may not be drawn to scale.

DETAILED DESCRIPTION

Figure 1A:
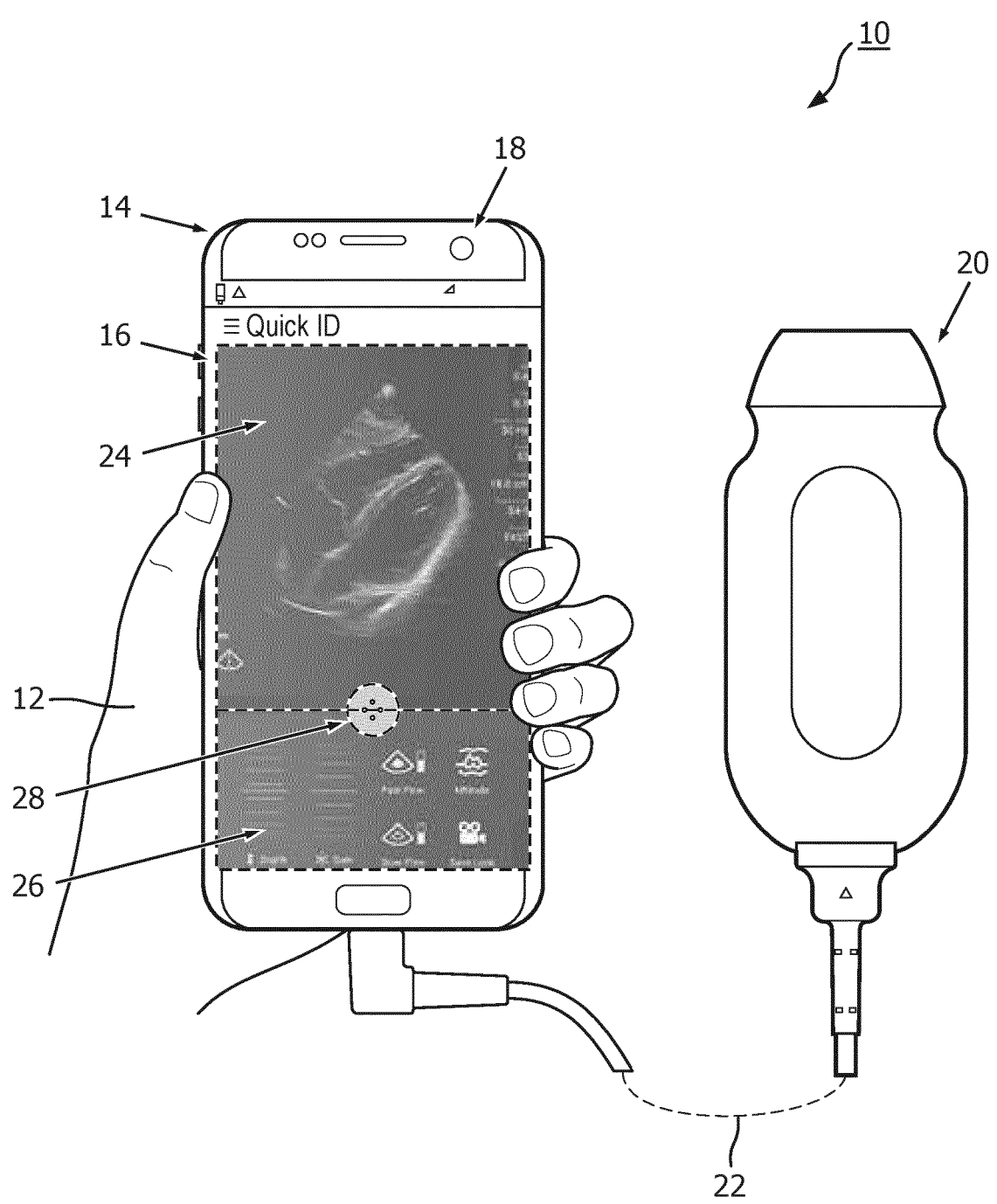
FIGS. 1A and 1B are front and rear views, respectively, of an ultrasound portable system with deep learning-based real-time eye-gaze tracking for use by a device operator according to an embodiment of the present disclosure.

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

Figure 1B:
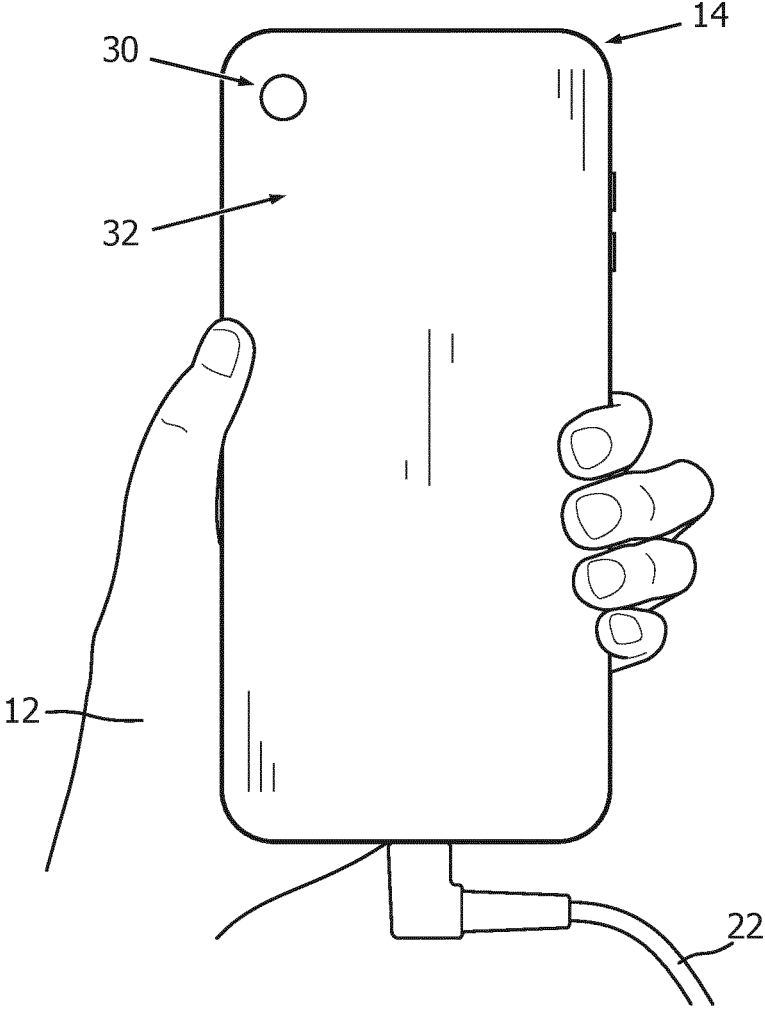

With reference now to FIGS. 1A and 1B, there are shown front and rear views, respectively, of an ultrasound portable system 10 with deep learning-based real-time eye-gaze tracking for use by a device operator 12 according to an embodiment of the present disclosure. As shown in FIG. 1A, the ultrasound portable system 10 comprises a smart device 14 having at least a display 16 and a camera 18 having a fixed spatial relationship to the display 16. Smart device 14 may comprise a smart phone (e.g., an iPhone™ or similar type mobile phone), tablet (e.g., an iPad™ or similar type tablet device), or any other suitable mobile device configured with at least a controller, software, a user interface, front/back cameras, and voice recording capabilities to perform various actions and functions, as discussed herein with respect to various embodiments of the present disclosure.

For example, the smart device 14 includes at least a controller that may comprise one or more of microprocessors, microcontroller, field programmable gate array (FPGA), integrated circuit, discrete analog or digital circuit components, hardware, software, firmware, or any combination thereof, for performing various functions as discussed herein, further according to the requirements of a given portable ultrasound system/device implementation and/or application. The controller may further comprise one or more modules, or various combinations of the one or more modules, for performing various functions as discussed herein, further according to the requirements of a given ultrasound portable system/device implementation and/or application. It is understood that the modules may be computer program modules which are rendered in a non-transitory computer-readable medium.

In one embodiment, camera 18 comprises a front-facing camera that is communicatively coupled to the smart device 14. For example, the camera 18 can comprise a built-in camera on the smart device 14 of the ultrasound portable system 10. In another embodiment, the camera 18 may comprise any type of sensing device, currently known or developed in the future, e.g., mono-, stereo-camera, time of flight (ToF), infrared, or other sensory data device from which gaze and eye movement can be extracted. The ultrasound portable system 10 further comprises an ultrasound probe 20 communicatively coupled to the smart device 14, for example, via signal cable 22 plugged into a port on the smart device 14, or via suitable wireless communication. The smart device 14 is configured to acquire ultrasound images, via the ultrasound probe 20 over a period of time, wherein the period of time includes at least a portion of an ultrasound scan protocol and/or ultrasound exam. The smart device 14 is further configured to: present, via at least the display 16, at least one ultrasound image of the acquired ultrasound images in an image space portion 24 of the display 16; acquire digital images, via the camera 18 over the period of time, wherein an image content within a field of view (FOV) of the camera 18 includes at least the device operator's head pose, and left and right eyes within respective digital images. In one embodiment, the digital images which capture the device operator can be de-identified, as appropriate, to eliminate privacy issues and/or concerns in connection with a device operator. The smart device 14 is further configured to determine or predict eye-gaze focus point locations on the smart device within at least (i) the image space portion 24, (ii) a control space portion 26, or (iii) a combination of the image space and control space portions of the display 16 relative to the camera 18, via an image processing framework or a deep learning framework, as will be discussed further herein. For instance, gaze and eye movements are used to predict an eye-gaze focus point location on the smart device in an ultrasound image being presented in the image space portion 24 of the display 16 (e.g., the user is looking top right which correspond to the atrial chamber) or in the control space portion 26 (e.g., containing soft buttons for mode transition and/or making a diagnostic ultrasound measurement). Also included on the display 18 is a command soft button 28, as will also be discussed further herein.

Referring still to FIGS. 1A and 1B, the smart device 14 can further include wherein the camera of the smart device comprises both a front-facing camera 18 on a front side of the smart device 14 (FIG. 1A) and a rear-facing camera 30 on a rear side 32 of the smart device 14 (FIG. 1B). Each of the front-facing camera 18 and the rear-facing camera 30 have a respective fixed spatial relationship to the display 18 on the front side of the smart device 14. The front-facing camera 18 comprises a camera for acquiring digital images of the device operator 12 within the front-facing camera's field of view (FOV), and more particularly, the device operator's head pose, and right and left eyes. The smart device 14 can be further configured to acquire rear-facing digital images, via the rear-facing camera 30, and more particularly, digital images of at least the ultrasound probe 20 within a field of view (FOV) of the rear-facing camera 30. A content of the rear-facing digital images can include at least a pose of the device operator's hand, or a pose of the ultrasound probe 20, within respective rear-facing digital images.

Figure 2:
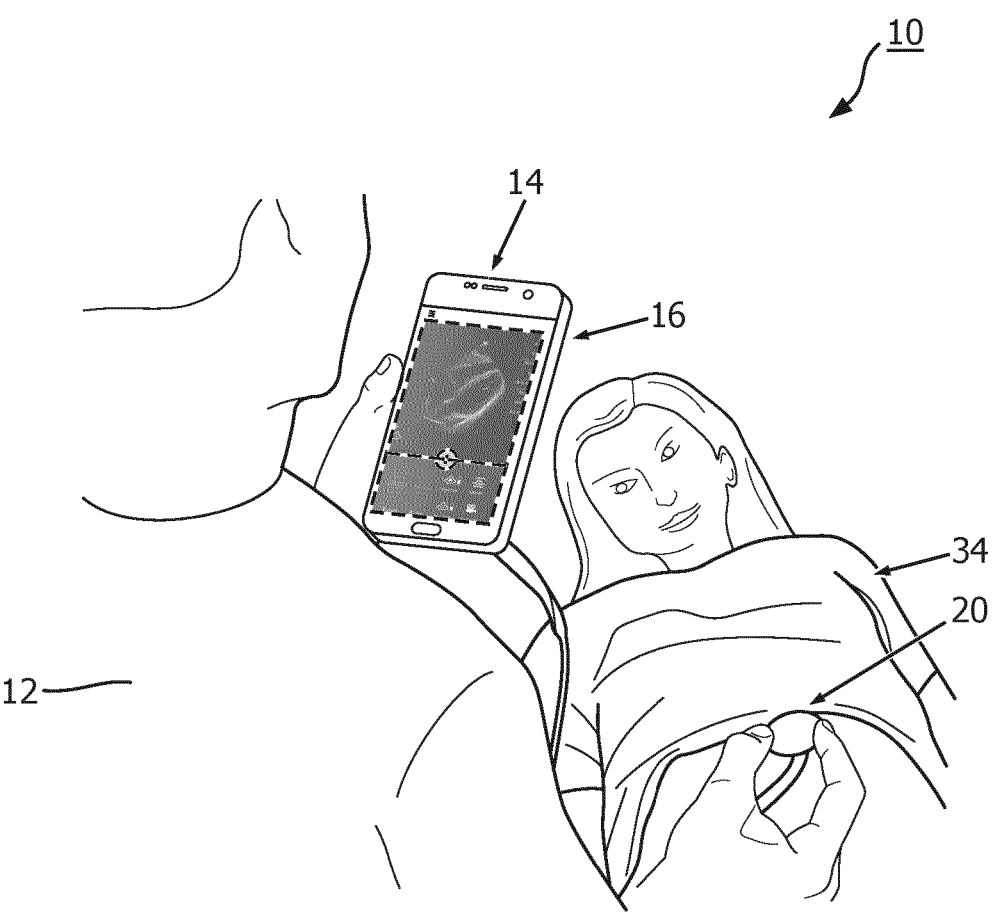
FIG. 2 is an illustrative view of an ultrasound portable system with deep learning-based real-time eye-gaze tracking for use by a device operator according to another embodiment of the present disclosure.

Turning now to FIG. 2, there is shown an illustrative view of an ultrasound portable system 10 with deep learning-based real-time eye-gaze tracking for use by a device operator 12 according to an embodiment of the present disclosure. As can be understood, ultrasound portable systems can be used in a variety of different settings, and are of particular importance in emergency situations. Portable ultrasound systems feature two main components, (i) an intelligent agent or smart device and (ii) an ultrasound probe communicatively coupled to the intelligent agent or smart device. The intelligent agent or smart device of the portable ultrasound system is often held in one of the device operator's hands (or can be set on a stand), while the ultrasound probe is held in the device operator's other hand. As will become apparent, the embodiments of the present disclosure use machine learning and deep learning techniques to advantageously support novice and expert users (i.e., device operators) during ultrasound scanning examinations with ultrasound portable systems.

The smart device 14 shown in FIG. 2 is that of a smart tablet device, being held in the left hand of the device operator 12, while the ultrasound probe 20 is being held in the right hand of the device operator. The ultrasound probe 20 is operatively coupled to the smart device 14 during an ultrasound exam being performed on a region of interest of the patient 34. The device operator 12 may look upon the display 16 on the front-side of the smart device 14 and/or upon the ultrasound probe 20 placed upon the patient 34, as appropriate, during a given ultrasound scan protocol and/or ultrasound exam.

In operation, the method comprises acquiring ultrasound images, via the smart device 14 and the ultrasound probe 20, over a period of time. The period of time includes at least a portion of the given ultrasound scan protocol and/or ultrasound exam. The method further comprises presenting, via at least the display 16, at least one ultrasound image of the acquired ultrasound images in an image space portion 24 of the display 16. Digital images are acquired, via the camera 18 over the period of time, wherein an image content within a field of view of the camera 18 can include at least the device operator's head pose, and left and right eyes within respective digital images.

Figure 3:
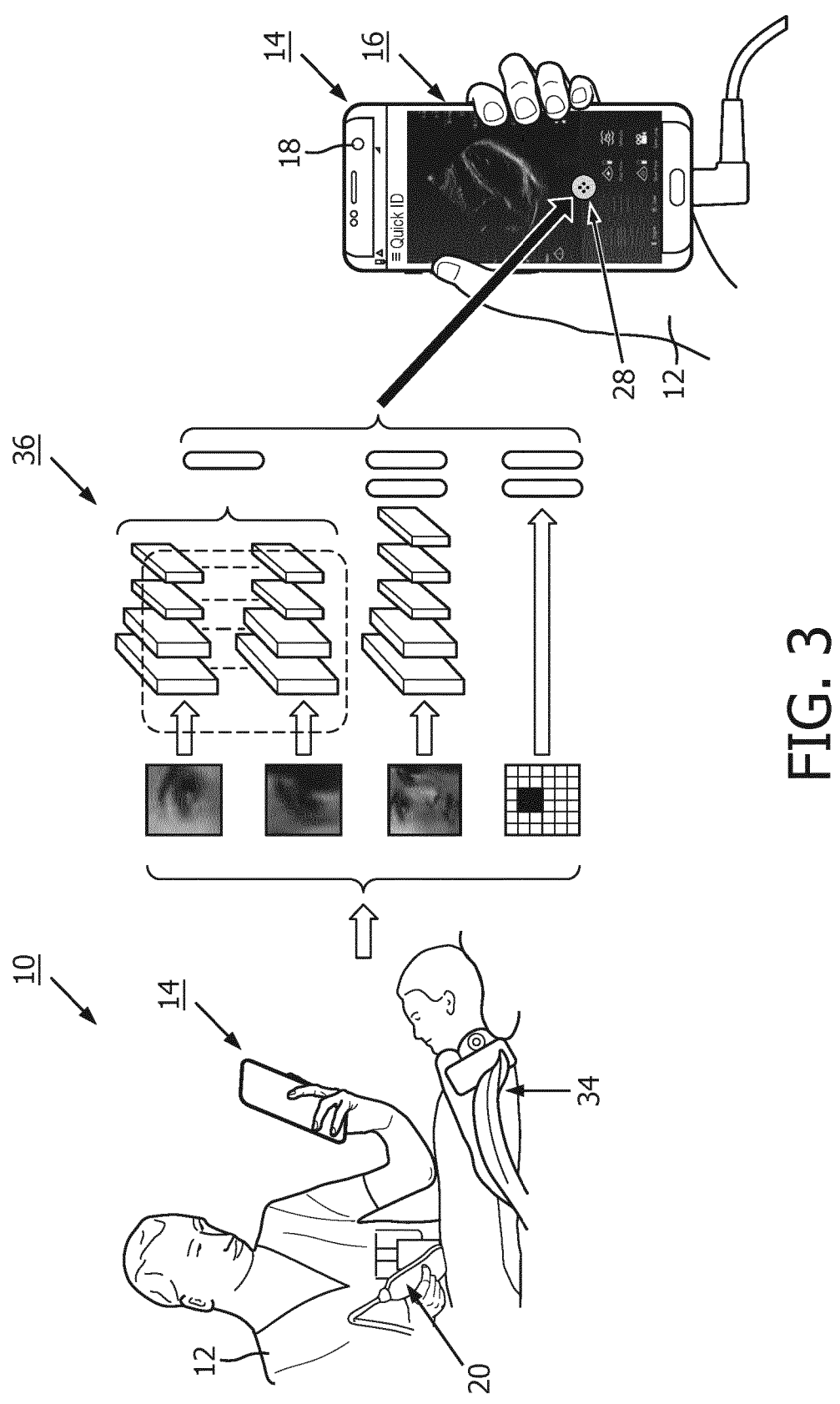
FIG. 3 is an illustrative view of a deep learning-based, real-time eye-gaze tracking, approach designed to command the ultrasound portable system according to an embodiment of the present disclosure.

With reference now to FIG. 3, there is shown an illustrative view of a deep learning-based, real-time eye-gaze tracking, approach designed to command the ultrasound portable system 10 according to an embodiment of the present disclosure. The device operator 12 in FIG. 3 is shown holding the smart device 14 in the device operator's left hand, while holding the ultrasound probe 20 in the device operator's right hand. The ultrasound probe 20 is coupled to the smart device 14 during an ultrasound exam being performed on a region of interest of the patient 34. The device operator 12 may look upon the display 16 on the front-side of the smart device 14 and/or upon the ultrasound probe 20 placed upon the patient 34, as appropriate, during a given ultrasound scan protocol and/or ultrasound exam.

As previously discussed, the usage of accessories to station (i.e., to place or to hold stationary) the intelligent agent or smart device (e.g., smart phone or tablet) of the ultrasound portable system during image acquisition or capture per a given scanning protocol is very limited. This is especially true with respect to ultrasound portable systems used in emergency settings where real-time capture and diagnosis is needed. To overcome such a problem, the embodiments of the present disclosure provide a method that comprises the use of gaze and eye tracking with deep learning to support device operators using the ultrasound portable system in carrying out scanning protocols and a corresponding ultrasound image acquisition per the scanning protocols.

Gaze and eye tracking have applications in many areas and they represent the ultimate way of interaction between humans and computers. Gaze indicates the human visual attention while eye movement provides rich information underlying a person's thoughts and intentions. There are many external devices available on the market that allow screen-based eye tracking (i.e., desktop) along with wearable glasses (e.g., Eye Tribe, Tobii EyeX, iMotions, etc.). These conventional eye-gaze tracking techniques rely on the use of tracking devices to integrate the eye and head position to compute the location of the gaze on the visual scene.

To overcome the need of adding external devices in already critical settings in emergency situations for both device operators and patients, the system and method of the present disclosure may adopt as one embodiment of an image processing algorithm a deep learning framework (generally indicated by reference numeral 36 in the Figures) that takes as input the device operator's gaze and eye movement to determine or to predict a point location (i.e., an eye-gaze focus point location (x,y)) on the smart device 14 of the ultrasound portable system 10. The determined or predicted eye-gaze focus point location is within the display 16, and more particularly, within one or both of the image space portion 24 of display 16 (e.g., an ultrasound image space) and/or the control space portion 26 (e.g., a graphical user interface space). In one embodiment, the determined or predicted eye-gaze focus point location on display 16 may correspond with the command soft button 28 and is used to command the ultrasound portable system in performing a particular function, as discussed further herein. Other embodiments of image processing framework are contemplated herein which may include, for example, a detection algorithm (for which AI not necessary) that works on the images acquired by the camera for eye-gaze tracking. The detection algorithm may involve machine learning, image processing and mathematical algorithms to determine the eye's position and gaze point, as known in the art. In addition, deep learning may not be needed for determining eye-gaze tracking; however, a deep learning framework or AI network as discussed herein may generate attention maps, classify the type of attention map and then subsequently run prediction and guidance tasks.

With respect to using an ultrasound portable system, expert users may quickly focus attention to only part of a captured or acquired ultrasound image, instead of processing the whole scene in an ultrasound image space. The ability to track a device operator's eye movement could provide valuable insights, since ideally one could predict a device operator's intentions based on what he or she is looking at or focused on, at a given point in time of an ultrasound exam. Gaze tracking has been used in the past, for instance, to allow eye typing.

Visual attention prediction or visual saliency detection is a classic research area in the field of computer vision that allows image cropping, object detection, and many more applications. Saliency maps represent images where the highlighted (i.e., salient) features represent the human eye predicted focus locations. Several approaches have been developed in the past to infer the human attention with and without knowledge of image content, but tracking the human gaze and eyes became feasible only in the recent years because of the use of Convolutional Neural Networks (CNNs) and deep learning architectures. The attention/saliency maps generated by CNNs predictions, can represent the semantic information within an ultrasound image (i.e., captured or acquired ultrasound image) and lead a device operator to eventually take action, for instance during a scanning protocol (e.g., freeze image), or in a review mode when a specific frame has to be picked out of a loop of B-mode images for subsequent measurements (i.e., diagnostic ultrasound image measurements).

Recent success in deep learning frameworks for eye-gaze tracking has been demonstrated and has shown that, without the need of external devices, deep learning is able to track the eyes and gaze movement of over 1,000 subjects to predict where on their iPhone™ and iPad™ they were looking at. On the same trend, leveraging the current state-of-art, the embodiments of the present disclosure make use of CNNs to separately train head pose, gaze, left and right eye to predict a point location (i.e., an eye-gaze focus point location (x,y)) that identifies where the device operator's attention is focused on the ultrasound portable device 10 (i.e., within one or both of the image space portion 24 of display 16 (e.g., an ultrasound image space) and/or the control space portion 26 (e.g., a graphical user interface space). This approach does not require a pre-existing system for head pose estimation or any other engineered features (i.e., external devices) for prediction. Separate convolutional neural networks will be used to train the eyes (left and right eye tracking), gaze, and the head pose. The output of this cascade of CNNs is reorganized into fully connected (FC) layers representing the feature vectors of the separate trainings. These FC layers are merged together to predict a point location of coordinates (x,y) on the display 16 of the smart device 14, as will be discussed further herein.

To memorize what is the action taken by sonographers (i.e., device operators) behind their eyes movement, one embodiment makes use of long-short term memory (LSTM) networks or recurrent neural networks (RRN). The use of LSTM networks or RRN networks will help memorize which is the "command" for a given track/path of the eyes (as will be discussed further with reference to FIG. 4). As the ultimate goal is to command the ultrasound portable system, the embodiments of the present disclosure can utilize the features (or feature vectors) from the cascade of CNNs, as long as the set of coordinates of a given attention/saliency map define which further action is taken.

Figure 4:
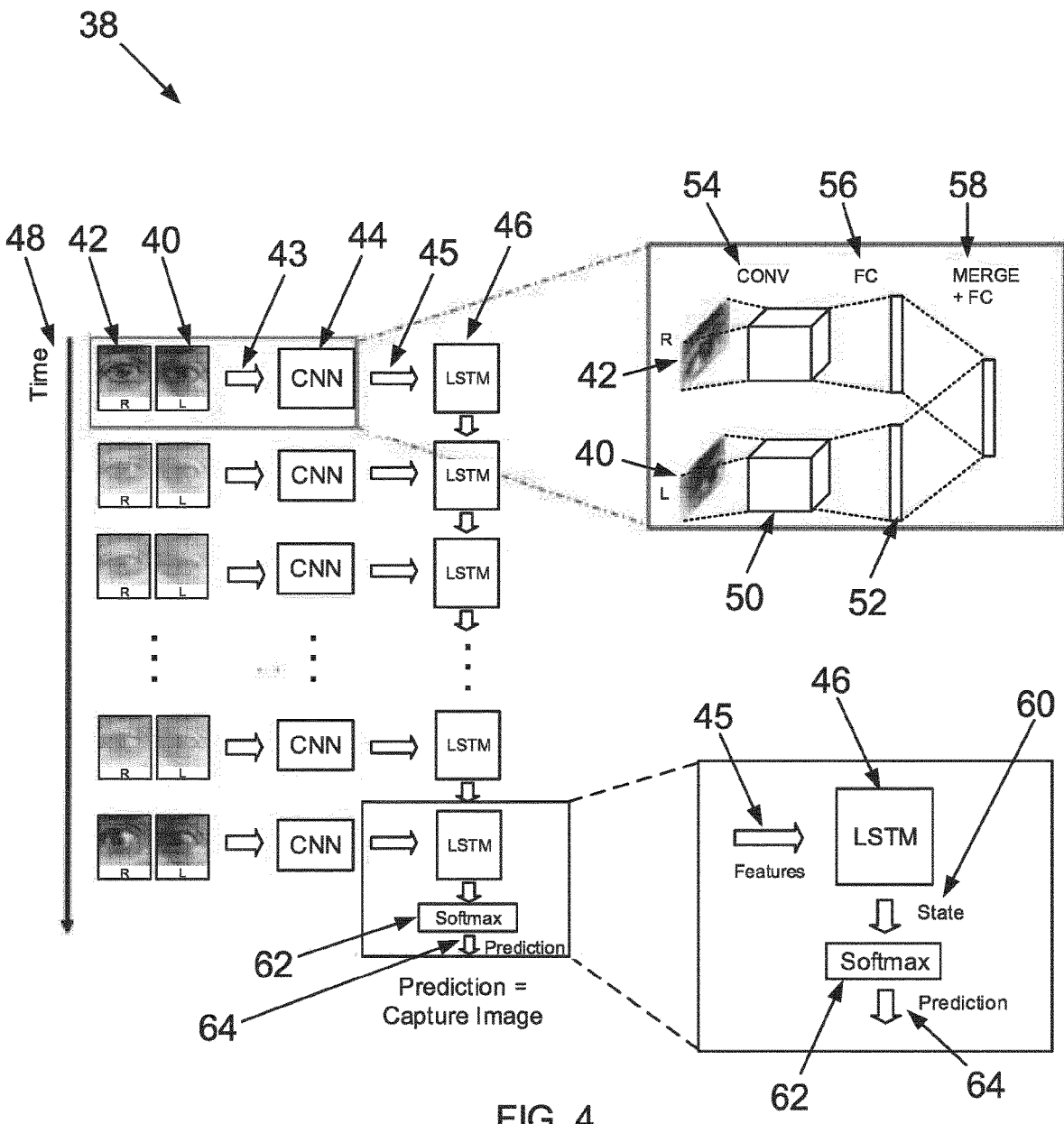
FIG. 4 is a diagram view of eye tracking for the left and right eye carried out in parallel, a cascade of Convolution Neural Networks (CNNs) for each eye which lead to a prediction of a focus point location (x,y) on the screen, and instances of retrieving temporal information and complete eye movement via long-short term memory (LSTM) networks and/or recurrent neural networks (RRN) architectures in the method for deep learning-based real-time eye-gaze tracking for an ultrasound portable system according to an embodiment of the present disclosure.

With reference now to FIG. 4, there is shown a diagram view of eye tracking 38 for the left and right eye (indicated via reference numerals 40 and 42, respectively) carried out in parallel, a cascade of Convolution Neural Networks (CNNs) 44 for each eye which lead to a prediction of a focus point location (x,y) on the display 16, and instances of retrieving temporal information and complete eye movement via long-short term memory (LSTM) networks 46 and/or recurrent neural networks (RRN) architectures. A given track/path of the eyes is determined utilizing the cascade of CNNs and LSTM networks at discrete instances over time 48 to predict a given command 64 (e.g., capture image) to be executed on the ultrasound portable system 10. At each instance, separate images (one image for the right eye 42, one image for the left eye 40) are input, indicated by reference numeral 43, to the cascade of CNNs 44. The cascade of CNNs include a first convolution block (CONV) 50 which receives as input the image of the left eye 40, and the output of the first convolution block 50 is input to a first fully connected block (FC or Flatten) 52. Similarly, a second convolution block (CONV) 54 receives as input the image of the right eye 42, and the output of the second convolution block 54 is input to a second fully connected block (FC or Flatten) 56. The outputs of the first and second fully connected blocks 52 and 56, respectively, are input to a merged and fully connected block (Merge+FC) 58. The output of the merged and fully connected block 58 comprises a feature (or feature vector) set 45 of coordinates representative of a point location (x,y) on the display 16 of the smart device 14 for a respective instance. In one embodiment, the input images (40, 42) comprise digital images, each having dimensions of e.g., 24×24×1, the CONV layers (50, 54) comprise layers, each having dimensions e.g., 24×24×16, the FC layers (52, 56) comprise layers, each having a dimension of e.g., 128, and the Merge+FC layer 58 comprises a layer having a dimension of e.g., 128.

With reference still to FIG. 4, LSTM networks 46 or RRN networks will help memorize which feature (or feature vector) set 45 of coordinates representative of an eye-gaze focus point location (x,y) on the display 16 of the smart device 14 for each respective instance. The output state 60 of the LSTM 46 (i.e., at the last instance which is representative of a collection of predicted point locations over time) is processed via Softmax 62. The output of Softmax 62 is a "command" prediction 64. That is, the Softmax 62 output is a predicted "command" for a given track/path of the eyes as determined from the collection of predicted eye-gaze focus point locations over time. Softmax functions handle multi-class logistic regression and classification; hence, the predicted command is selected from multiple command choices and it represents the one with highest confidence score (i.e., probability). In FIG. 4, the prediction is the command to "Capture Image" in a given ultrasound scan protocol.

For example, expert sonographers may focus their attention on cardiac valves and chamber contours before capturing B-mode images and reutilizing the captured B-mode images in review mode. This process of focusing attention before capturing images includes the user's gaze and the eyes having to focus on cardiac features before a B-mode ultrasound image is saved. In the approach of the method and system of the present disclosure, this information obtained via expert sonographers can be utilized to train a deep learning network whose outcome could lead, for instance, to auto-save images without the need for the user (or device operator) to physically touch the display of the smart device to save images. In addition to cardiac related ultrasound images, the action of freezing and then acquiring ultrasound images based on the "sharpness" of anatomical landmarks on the ultrasound images can be applied to liver, kidney, thyroid and many other clinical applications.

Figure 5:
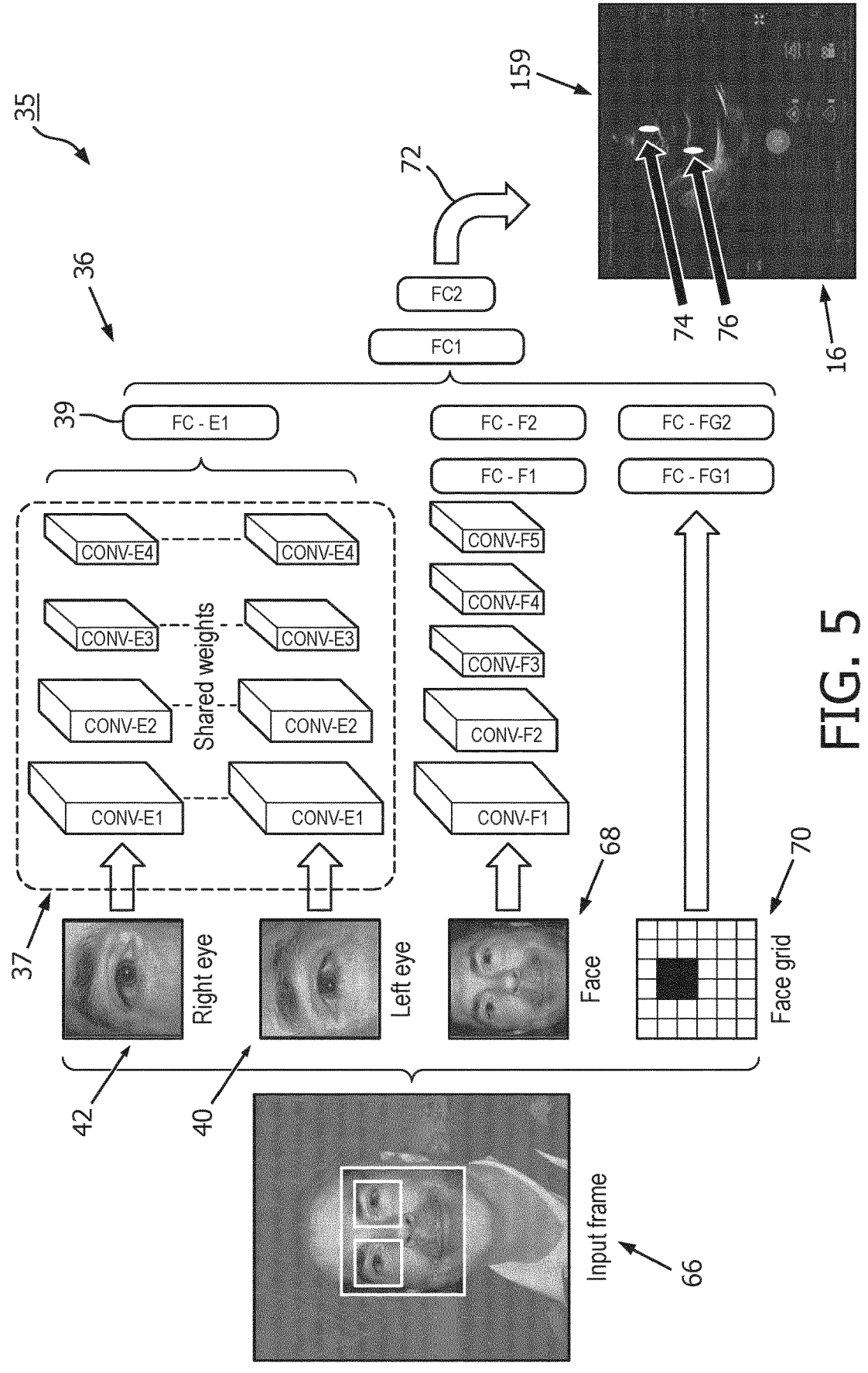
FIG. 5 is a flow-diagram view of deep learning-based real-time eye-gaze tracking as used in the method and ultrasound portable system according to various embodiment of the present disclosure.

With reference now to FIG. 5, there is shown a flow-diagram view 35 of one example of a deep learning-based real-time eye-gaze tracking framework 36 as used in the method and ultrasound portable system according to various embodiment of the present disclosure. The embodiment as shown in FIG. 5 includes training separate CNNs to predict a focus point location of coordinates (x,y) on the display 16 of the ultrasound portable system 10. The deep learning-based real-time eye-gaze tracking framework 36 utilizes training inputs and provides training outputs as a function of the inputs.

Deep learning is a sub-field of machine learning that tries to resemble the multi-layered human cognition system. One example of deep learning-based algorithms is a convolution neural network (CNN), a powerful artificial neural network technique, which is known in the art and only briefly described herein. The deep learning-based architecture of the CNN is used herein due its ability to preserve spatial (and temporal for 3D CNNs) relationships when filtering input images. A schematic diagram of a convolutional neural network 36 is shown in FIG. 5. With reference to FIG. 5, CNN 36 may take input images of raw pixels (e.g., images of the left eye 40, right eye 42, face 68, and face grid 70) and transform them via convolutional (CONN) layers, generally indicated by reference numeral 37 and then are fed into fully connected (FC) layers, generally indicated by reference numeral 39, which assigns probabilities or classes to categorize the inputs into a predicted focus point location. Pixels in an image can be processed by a different weight in a fully connected layer, or alternatively, every location can be processed using the same set of weights to extract various repeating patterns across the entire image. In the embodiments of the present disclosure, processing of the images of the left and right eyes utilizes shared weights. These trainable weights are referred to as kernels or filters; and are applied using a dot product or convolution and then processed by a nonlinearity function. Each convolutional layer may have several filters to extract multiple sets of patterns at each layer.

Training inputs to the deep learning network include B-mode images (not shown), digital images, and a face grid. With respect to the B-mode images, a separate deep learning network is trained to learn features (i.e., image features) on the B-mode images. For example, the deep learning network can learn to detect cardiac valves on cardiac ultrasound B-mode images. B-mode images other than cardiac related are also contemplated.

Referring again to FIG. 5, with respect to the digital images, the camera (e.g., the front-facing camera 18 on a front of the smart device 14 of the ultrasound portable system 10) can be used to acquire digital images from which to extract from each digital image input frame 66, the following: (i) one image 68 for the gaze, and (ii) two separate images, 40 and 42, respectively, for the left and right eyes for parallel prediction trainings. The eyes are included as separate individual inputs into the network (even though the face image already contains them) to provide the network with a higher resolution image of each eye to allow the network to identify subtle changes. A face grid 70 is utilized to reconstruct a head pose within a space of each digital image input frame 66, wherein the face grid input is a binary mask used to indicate the location and size of a user's head within the digital image input frame (e.g., of size 25×25).

Training outputs, indicated via reference numeral 72, include a training output of merged and fully connected (FC) layers that correspond to predicted focus point locations (x,y) on the display 16 of the smart device 14 of the ultrasound portable system 10. For example, a first predicted "focus" point location in an image space (within the ultrasound image) on the display 16 is indicated via reference numeral 74 and a second predicted "focus" point location in the image space on the display 16 is indicated via reference numeral 76.

Referring still to FIG. 5, as discussed, inputs include images of the left eye 40, right eye 42, and face 68 detected and cropped from the original frame 66 (e.g., having a size 224×224). The face grid 70 input is a binary mask used to indicate the location and size of the head within the frame (of size 25×25). The output can comprise a distance, in centimeters, from the camera, expressed as a focus point location (x,y) on the display 16. In one embodiment, with respect to the deep learning framework CNN 36 for eye tracking, CONV (indicated by reference numeral 37) represents convolutional layers (e.g., CONV-E1, CONV-F1, CONV-E2, CONV-F2, CONV-E3, CONV-F3, CONV-E4, CONV-F4) while FC (indicated by reference numeral 39) represents fully-connected layers (e.g., FC-E1, FC-F1, FC-F2, FC-FG1, FC-FG2, FC1, and FC2). Other CNN network configurations may also be applicable for use, in which filter sizes, number of layers and any other training parameter on the CNNs can vary based on the dataset and the different tasks to be achieved.

Figure 6:
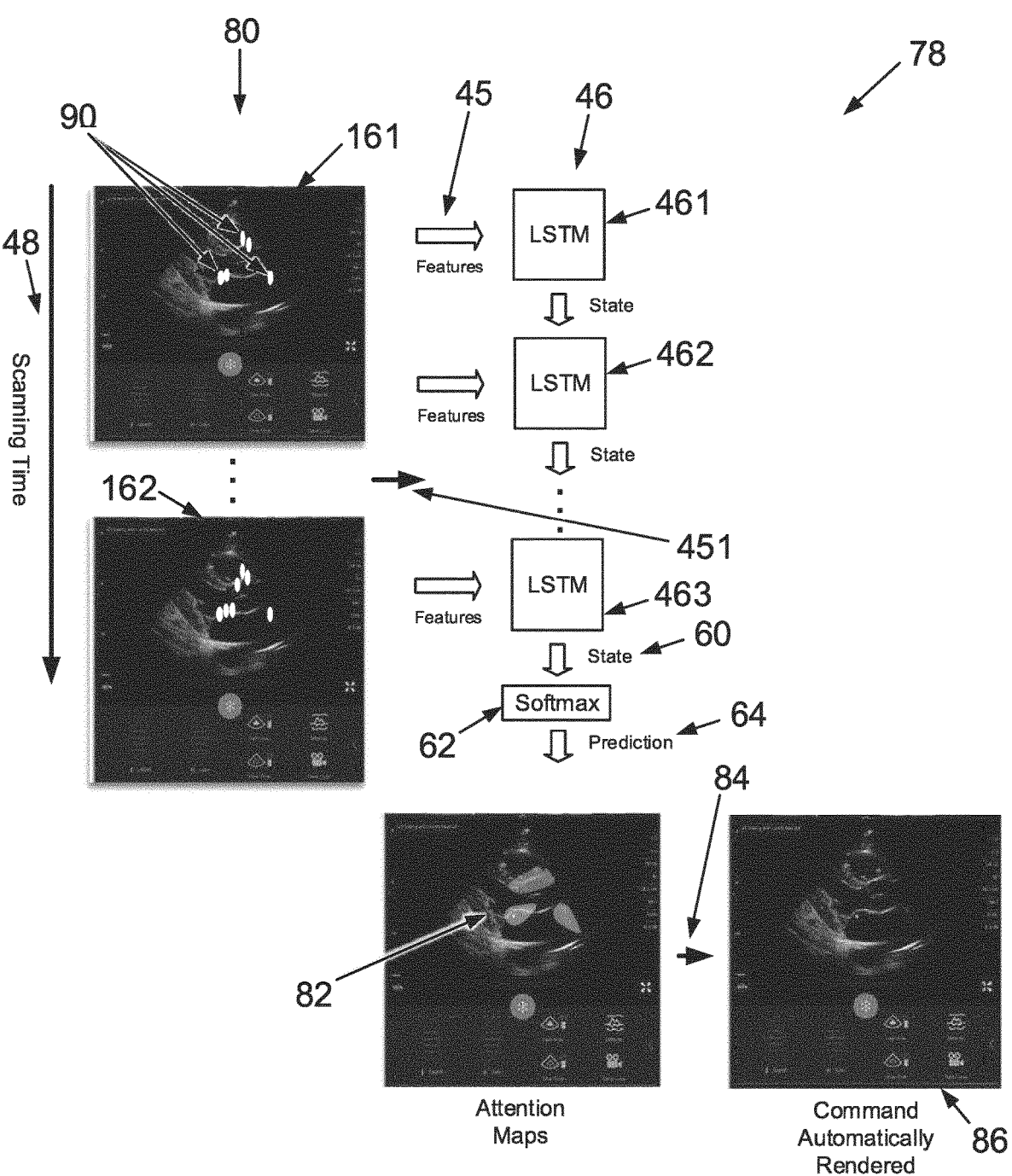
FIG. 6 is a flow-diagram view of predicted focus point locations and retrieval of complete eye movements per path for generating attention maps and predicted actions to command the ultrasound portable system according to an embodiment of the present disclosure, in which portions of the flow-diagram view are reproduced in FIGS. 6.1 and 6.2 for clarity.

With reference now to FIG. 6, there is shown a flow-diagram view 78 of predicted focus point locations and retrieval of complete eye movements per path for generating attention maps and predicted actions to command the ultrasound portable system 10 according to an embodiment of the present disclosure. Portions of the flow-diagram view 78 of FIG. 6 are reproduced in FIGS. 6.1 and 6.2 for clarity. The method and system of the present disclosure utilize a sequence 80 of determined or predicted eye-gaze focus point locations 90 of respective coordinates (x,y) on the display 16 of the smart device 14 over time 48 (i.e., scanning time) to predict a command 84 to be executed by the ultrasound portable system 10 (e.g., the predicted command may be to save the fifth and tenth images from a set of images in a B-mode cine loop for further diagnostic measurements in review mode). Training inputs to the deep learning network can include (i) determined or predicted eye-gaze focus point locations 90 and/or (ii) a temporal accumulation (161, . . . , 162) of the determined or predicted eye-gaze focus point locations. Training outputs can include actions to take 86 (i.e., based on the predicted command 84 to be executed) and/or a predicted sequence of actions. In one embodiment, gaze and eye movements can be tracked during an entire duration of the scanning protocol to output attention maps (i.e., accumulation of focus point locations in an ultrasound image presented on the display) for the duration of the ultrasound image acquisition.

The sequence 80 of predicted points 90 (i.e., eye-gaze focus point locations) of respective coordinates (x,y) on the display 16 are accumulated over time 48 (e.g., a period of time corresponding to a given ultrasound image acquisition/ exam duration per a given scanning protocol). These accumulated sequence (161, . . . , 162) of points of respective coordinates (x,y) will define a path. In other words, a sequence of determined or predicted points (161, . . . , 162) of respective coordinates (x,y) accumulated over time 48 is used to define a path. This path is labelled or identified with the action taken by expert sonographers (ground truth), e.g., where the expert sonographer freezes the image after checking to confirm that a cardiac ultrasound image has sharp contours. The temporal accumulation of determined or predicted points (161, . . . , 162) of respective coordinates (x,y) on the ultrasound image presented via the display 16 are output (i.e., collectively indicated via prediction arrow 451) into long-short term memory (LSTM) networks 46 (i.e., respective ones of LSTMs (461, 462, . . . , 463)) and converted into one or more attention maps 82.

In obtaining each temporal accumulation of predicted points (161, . . . , 162), eye tracking can be carried out in parallel, via a cascade of Convolution Neural Networks (CNNs) for each eye which leads to the prediction of focus point locations (x,y) on the display 16, as indicated by reference numeral 90. Responsive to the of temporal accumulation of predicted points or predictions (i.e., collectively indicated via prediction arrow 451), temporal information and complete eye movement and gaze is retrieved via long-short term memory (LSTM) networks 46, for each instance in a sequence (461, 462, . . . , 463). In a manner as noted previously herein, a given track/path of the eyes and gaze is determined utilizing the cascade of CNNs and LSTM networks at discrete instances over time 48 to generated an attention map or maps 82 based on a prediction 64. A feature (or feature vector) set 45 of coordinates representative of the focus point locations (x,y) on the display 16, indicated by reference numeral 90, for a respective instance in time 48 are input to the LSTM network at respective instances, as indicated by reference numerals (461, 462, . . . , 463). The output state 60 of the LSTM 463 (i.e., at the last instance which is representative of a collection of predicted point locations over time) is processed via Softmax 62, which determines the predicted focus point location with a highest probability. As previously discussed, Softmax functions handle multi-class logistic regression and classification; hence, the prediction is selected from multiple prediction choices and it represents the one with highest confidence score (i.e., probability). The output of Softmax 62 is a prediction 64 which is converted into an attention map or maps 82. The attention map or maps 82 are a combination/ path of eyes movement and gaze over a period of time for scanning. The predicted attention maps 82 are then converted, as indicted via arrow 84, into "actions" (e.g., a capture image command).

As indicated with reference still to FIG. 6, training outputs can include actions to take 86 and/or a predicted sequence of actions. Actions to take 86 comprise one or more commands to be executed for a given combination/ path of eyes movement and gaze. The attention maps 82 (i.e., combination/path of eyes movement and gaze) are converted, at 84 in FIG. 6, into "actions" (commands). For instance, a novice user generates an attention map 82 that is "close" to the freeze command of expert sonographers (i.e., a freeze command attention map), so the ultrasound portable system 10 automatically captures that image (e.g., as discussed herein with reference to FIG. 3 and predicted focus point locations of respective coordinates (x,y) in the image space), via the smart device 14 and the ultrasound probe 20, without any need for the user or device operator to (i) interrupt the ultrasound exam and/or (ii) touch the display screen 16. In one embodiment, the command is automatically rendered subsequent to its prediction. As disclosed herein, gaze and eye tracking are thus used to initiate a command that can be automatically executed and/or suggested to the device operator for being executed (e.g., light up a Doppler soft button icon to suggest to the user to turn on Color-Doppler imaging for a given view, or to capture the certain view).

With reference to FIG. 6.1, the temporal accumulation 161 of predicted focus point locations 90 of FIG. 6 is shown in an enlarged view. An ultrasound image 88, e.g., obtained via smart device 14 and ultrasound probe 20, is presented within the image space portion 24 of the display 16. The ultrasound image 88 is further presented along with the predicted focus point locations 90 overlying the ultrasound image 88. Furthermore, a control space portion 26 of the display and a command soft button 28 are also shown on the display 16.

With reference now to FIG. 6.2, the attention map 82 of FIG. 6 is shown in an enlarged view. The attention map 82 includes one or more temporal accumulations of predicted focus point locations, e.g., indicated via reference numerals 92, 94, and 96, according to a given combination/path of eyes movement and gaze of a device operator for a given scanning time. As in FIG. 6.1, the ultrasound image 88 is presented within the image space portion 24 of the display 16, wherein the one or more temporal accumulations of predicted focus point locations, indicated via reference numerals 92, 94, and 96 overlie the ultrasound image 88. Furthermore, a control space portion 26 of the display and a command soft button 28 are also shown on the display 16.

Figure 7:
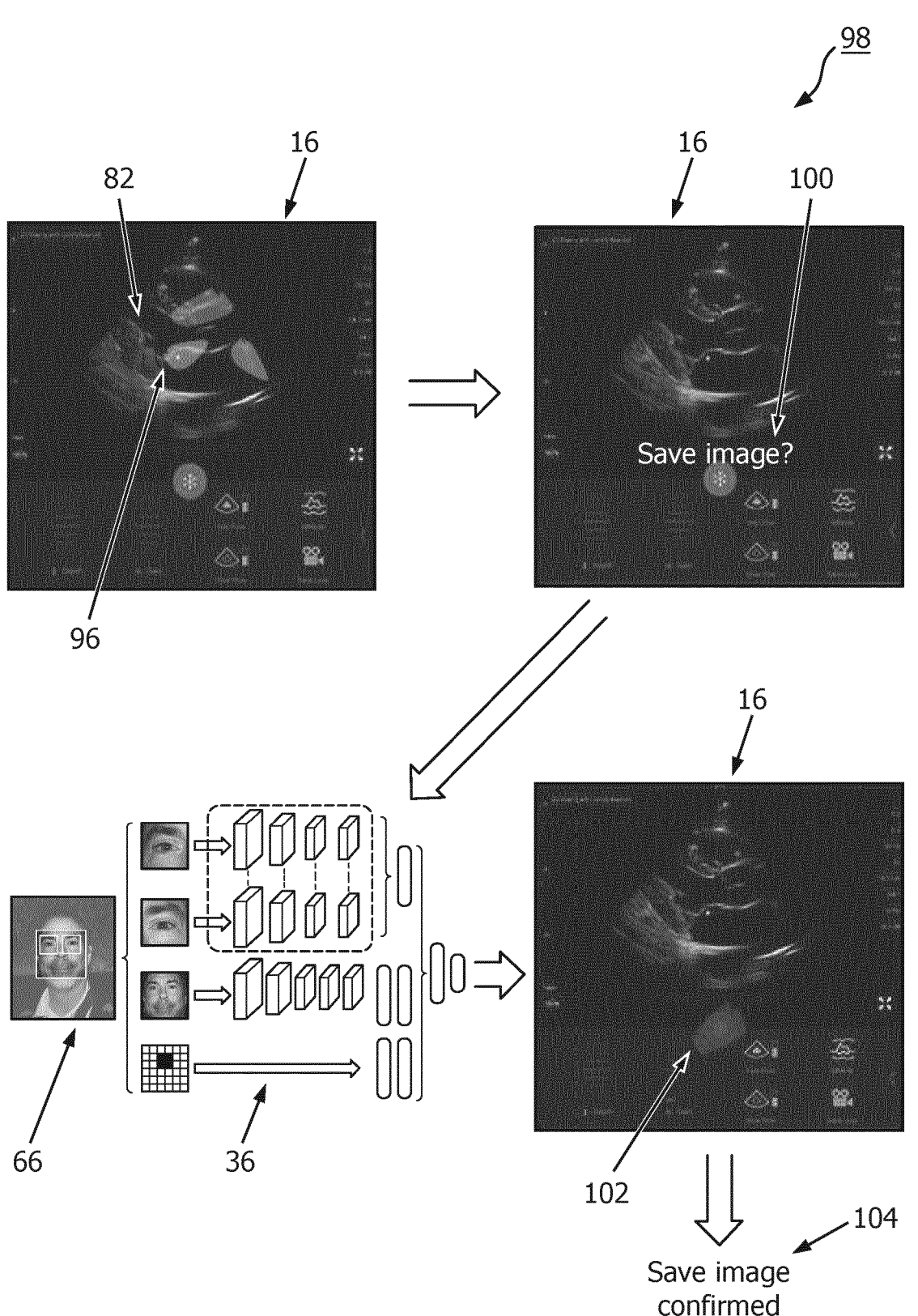
FIG. 7 is a flow-diagram view of eye-gaze tracking to confirm a command on the ultrasound portable system according to another embodiment of the present disclosure.

Turning our attention now to FIG. 7, there is shown a flow-diagram view 98 of eye-gaze tracking to confirm a command on the ultrasound portable system 10 according to another embodiment of the present disclosure. In particular, the flow diagram illustrates command confirmation prior to actual execution of the predicted command. In this embodiment, the device operator is given the freedom to confirm the predicted command via eye movement and gaze tracking, as discussed herein with reference to FIG. 6.

Eye-gaze tracking to confirm a command on the ultrasound portable system 10 begins with a prediction of the attention map 82 of temporal accumulations 92, 94, 96 of predicted focus point locations on the ultrasound image presented on display 16, as discussed herein with reference to FIGS. 6 and 6.2. Subsequent to the prediction of the attention map 82, a text overlay message 100 (e.g., "Turn on Color Doppler mode?", "Capture image?", etc.) is provided on the B-mode ultrasound images presented on display 16. The text overlay message 100 seeks for the device operator to confirm the predicted command/action before the predicted command/action is actually executed, via the smart device 14 and/or ultrasound probe 20. One main difference between the embodiment of FIG. 7 and the output in other embodiments disclosed herein is that the embodiment of FIG. 7 provides the device operator an opportunity to interact with the portable ultrasound system 10 to confirm and execute a predicted command.

Confirmation and execution of the predicted command is accomplished by the device operator looking at a high-lighted icon (e.g., soft button 28 or other suitable highlighted command icon) on the display 16 of the smart device 14. For instance, the user can confirm a capture of the ultrasound image by looking (i.e., via eyes movement and gaze) at a freeze button (i.e., the freeze image command soft button or icon), or a Color Doppler icon (e.g., to switch modes, from B-mode to Color Doppler mode). That is, subsequent to presentation of the overlay text message 100, the smart device 14 implements the deep learning framework for eye-gaze tracking 36 based on input images 66 to predict a location on the display 16 to which the device operator 12 is looking at. Upon predicting the location 102 on the display 16 that the device operator 12 is looking at corresponds with the soft button 28, the command is then executed. In this example, the "save image" command is confirmed and executed.

According to a further embodiment, the ultrasound portable system 10 utilizes eyes movement and gaze tracking 36 to define a level of assistance provided by the smart device 14 and/or estimate the experience of the user (i.e., estimate a user's level of experience, whether a novice user or an expert user, or somewhere in-between). The system estimates user experience by how scattered are the predicted focus point locations on the device during a given portion of an ultrasound scan protocol and/or exam. That is, the system estimates the user experience by a measure of how scattered the predicted focus point locations of respective coordinates (x,y) are on the ultrasound smart device 14 (in either one or both of the image space portion 24 and control space portion 26 of the display 16). Novice users tend to look around more than expert users that already know which features in the ultrasound image presented in the image space portion 24 of the display 16 to focus on and search on the respective ultrasound images for a given scan protocol and/or ultrasound exam. The inputs of this embodiment are the same as those used in the embodiment as discussed with reference to FIG. 5, but the output will influence the level of assistance and/or interaction between the device operator 12 and the smart device 14 (also referred to herein as an intelligent agent, i.e., a device with built-in intelligence and AI-aided solutions available on the device.)

For instance, if an expert user is predicted to be operating the ultrasound portable system 10, the smart device 14 (or intelligent agent) may choose to turn off or disable the predicted command confirmation mode embodiment and only activate the automatic execution of a predicted command or sequence of actions embodiment. Responsive to predicting that the device operator is an expert user, the smart device 14 may only activate the automatic execution of a predicted command or sequence of actions embodiment (e.g., which automatically saves images in the background while image acquisition continues according to the requirements of the given scanning protocol) by turning off or disabling the predicted command confirmation mode embodiment.

According to another embodiment, the ultrasound portable system 10 utilizes eyes movement and gaze tracking 36 for generating a command text report. Given the output of the embodiments relating to (i) predicted command action or sequence of actions to take (FIG. 6), and (ii) command confirmation (FIG. 7), respectively, the ultrasound portable system 10 can be further configured to generate a text report (i.e., a command report) explaining why one or more command was predicted, and/or why one or more particular predicted actions were taken. For example, the text report may comprise: "The image number 3 was saved because the attention was focused on cardiac walls and atrial valve.", "The Color Doppler mode was turned on because the attention was focused for 20 seconds on the left ventricle.", or other similar type explanation or report with one or more reasons for executing a particular predicted action.

Figure 8:
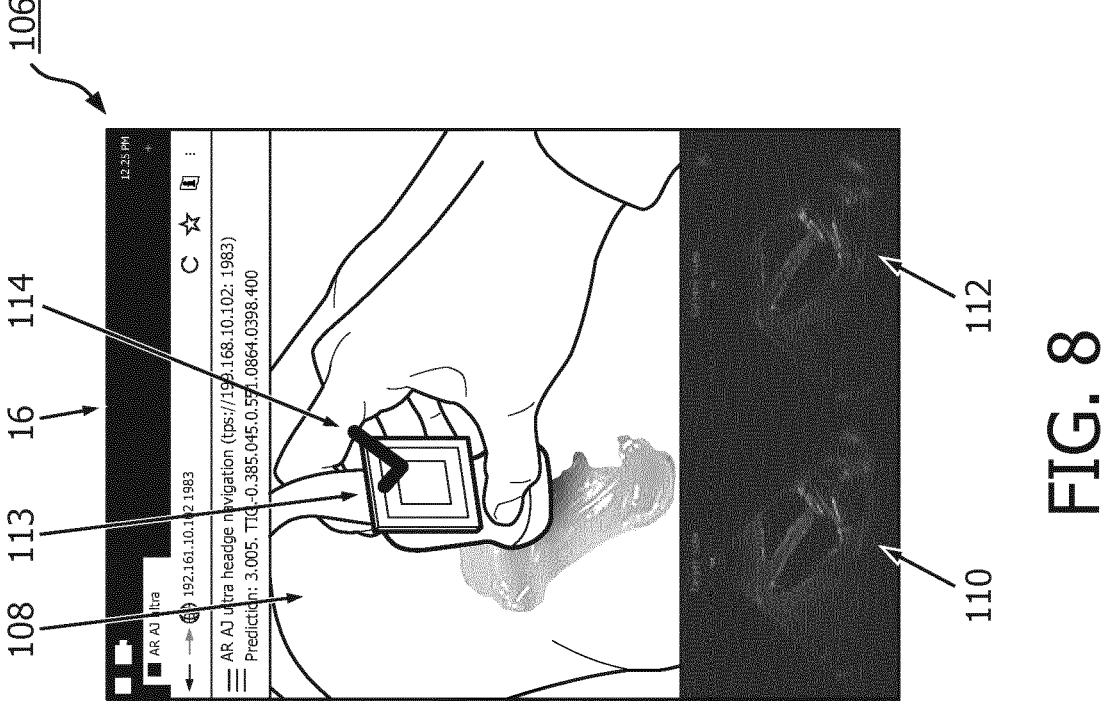
FIG. 8 is an exemplary display screen view of the ultrasound portable system showing augmentation of rear-view camera digital images with an augmented reality (AR) marker according to an embodiment of the present disclosure.

With reference now to FIG. 8, there is shown an exemplary display screen view 106 of the ultrasound portable system 10 showing augmentation of rear-view camera digital images 108 with an augmented reality (AR) marker 114 according to an embodiment of the present disclosure. In this embodiment, the ultrasound portable system 10 utilizes eyes movement and gaze tracking 36 to facilitate augmented reality. One example of a known ultrasound portable system is the Philips Lumify™ system, which operates with any suitable smart device such as a mobile phone or tablet. These mobile phone or tablet devices are usually equipped, in addition to a front-facing camera, with the back-facing monocular cameras.

According to an embodiment of the present disclosure, the ultrasound portable system 10 is configured to augment digital images captured the from rear-facing camera 30, and further configured to provide (i) additional feedback to the device operator 12, for instance, regarding the maneuvering of the ultrasound probe 20 or (ii) additional information provided from a remotely connected assistant. In one embodiment, the smart device is provided with an ability for, or has access to, remote calling of experts who are off-site at the time of an ultrasound exam for providing remote guidance to the device operator. Such additional feedback information is projected or overlaid on the digital images captured from the rear-facing camera 30, and presented on display 16, using a homography matrix at the location within the digital images of one or more tracked optical markers (e.g., a check box 113 on ultrasound probe 20) with unique patterns (e.g., a check mark or augmented reality (AR) marker 114), as known in the art.

As is also illustrated in FIG. 8, a target ultrasound image view 110 and a current ultrasound image view 112 can be presented on display 16. In this example, the additional feedback information (augmented reality AR marker 114) may confirm that the device operator 12 has the ultrasound probe 20 correctly positioned for a given scan protocol and/or ultrasound exam, in response to the current view 112 substantially matching the target view 110 within a desired degree of accuracy. In this manner, the device operator is advantageously notified by the ultrasound portable system 10 that the ultrasound probe 20 is correctly positioned near the target view, as indicated via the check mark or augmented reality AR marker 114.

Figure 9:
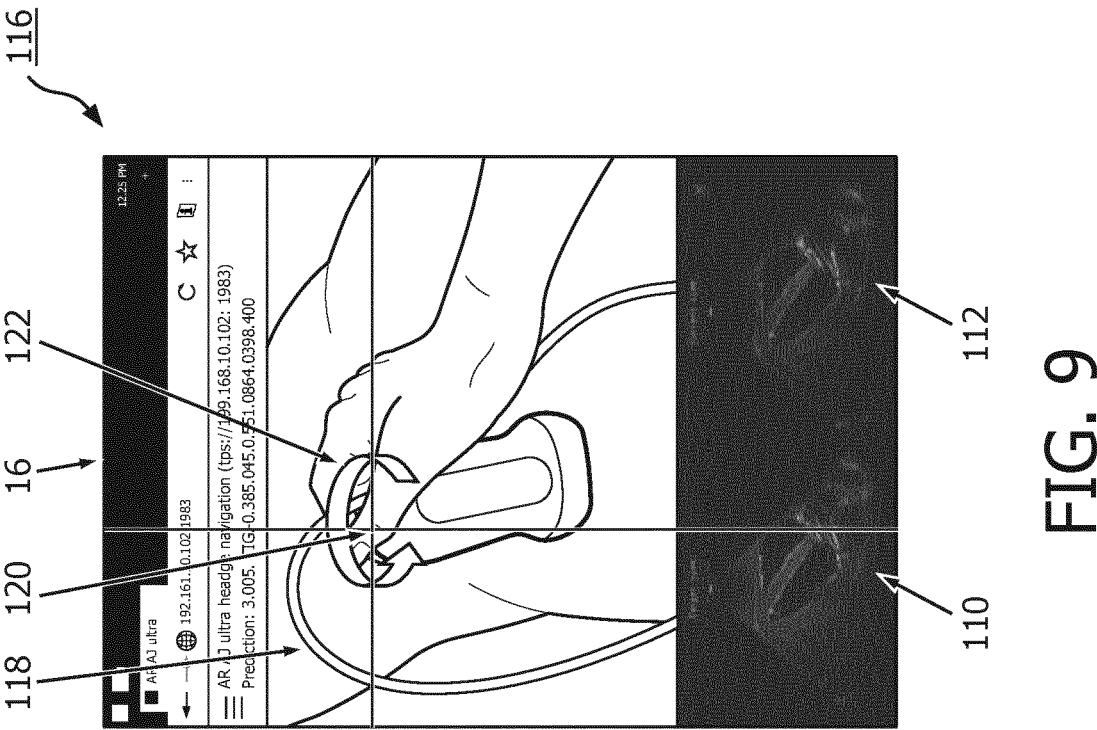
FIG. 9 is another exemplary display screen view of the ultrasound portable system showing augmentation of rear-view camera digital images based on focus point locations provided via eye-gaze tracking with the ultrasound portable system according to another embodiment of the present disclosure.

With reference now to FIG. 9, there is shown another exemplary display screen view 116 of the ultrasound portable system 10 featuring augmentation of rear-view camera digital image 118. The augmentation of rear-view camera digital image 118 is based on focus point locations provided via eye-gaze tracking according to an embodiment of the present disclosure. In this embodiment, the ultrasound portable system 10 is configured to augment the digital image 118 captured from the rear-facing camera 30, and to use predicted focus point location 120 coordinates (x,y) on the display 16 from the deep learning-based framework 36 for eye-gaze tracking, as previously discussed herein, in order to project the additional feedback information or augmented reality (AR) feedback information 122 at such predicted focus point location (x,y).

Referring still to FIG. 9, a target ultrasound image view 110 and a current ultrasound image view 112 can also be presented on display 16. Viewing the digital image 118 in FIG. 9, the augmented reality (AR) feedback arrow 122 is presented to advantageously assist the device operator 12 to position the ultrasound probe 20 during a given scan protocol and/or ultrasound exam for acquiring a current ultrasound image view 112 that substantially matches the target ultrasound image view 110, within a desired degree of accuracy. The augmentation of the digital image 118 with the AR feedback arrow 122 is based on the predicted focus point coordinates (x,y) provided from the deep learning-based framework 36 for eye-gaze tracking, as discussed herein with reference to FIG. 3. This marker-free approach of the augmentation of the rear-facing camera 30 digital images is not only easier to integrate into current ultrasound systems but it is also more robust to marker miscalibration errors and unintended displacement of the marker. In this example, the additional feedback information (augmented reality AR arrow 122) may assist the device operator 12 in correctly positioning the ultrasound probe 20 for a given scan protocol and/or ultrasound exam to substantially match the target view 110 within a desired degree of accuracy. Accordingly, the device operator is advantageously guided by the ultrasound portable system 10 for correctly positioning the ultrasound probe 20 to capture an ultrasound image in which the current ultrasound image view is near the target ultrasound image view.

In another embodiment, the ultrasound portable system 10 can be configured to implement a system calibration. Most of the currently known eye and gaze tracking wearable devices require some type of calibration, i.e., calibration is usually necessary to account for anatomical differences, such as orientation of eye's optical axis or presence of strabismus, in the expected user population. In this embodiment, a method for calibration of deep learning-based gaze tracking algorithm is described. To calibrate the deep learning-based gaze tracking algorithm of the present disclosure, the device operator can perform a sequence of steps as follows. The device user manually chooses a focus point location of coordinates (x,y) on the smart device 14 by tapping on the display screen. The deep learning-based eye-gaze tracking algorithm is started and an offset $(o_x, o_y)$ between estimated and defined point on the display 16 is calculated. The device operator repeats the process of manually choosing and tapping, and the eye-gaze tracking algorithm calculates the offset between the estimated and defined point on the display 16 a predetermined number of times until a given calibration according to system requirements is met. For instance, as soon as the device operator selects 20 points, an average offset $(ô_x, ô_y)$ between estimated and user-defined points is calculated. This average offset is consequently used during subsequent operation of the ultrasound portable system by the device operator. Alternatively, points which are manually selected by the user can be either used to fine-tune the deep learning-based gaze tracking algorithm model by retraining it with the new data points, or used as a reward function in a reinforcement type algorithm.

In yet another embodiment, the ultrasound portable system 10 can be configured to use device operator experience (e.g., an expert vs a novice) as an additional input. As discussed herein, in one embodiment, attention maps and device operator experience can be used to predict the intentions of the device operator, such as pressing of an ultrasound image freeze button. A novice device operator might have a different way of finding one or more particular features on the diagnostic ultrasound images presented in the image space portion 24 of the display 16 or controls on the user interface in the control space portion 26 of the display, compared to an expert device operator. To improve a prediction accuracy, in this embodiment, the ultrasound portable system 10 includes an additional input to the deep learning model for gaze prediction that takes into account and/or describes the experience of the device operator (i.e., a device operator user experience level). For instance, users can be graded into several categories (classes), such as resident (0), novice (1), experienced user (2), etc. An input vector, representative of the device operator experience level, could be processed by one fully connected (FC) layer of a CNN in the eye-gaze prediction deep learning-based framework, and then pointwise added to each point in one of the response map (left, right, or face branch) by tiling the output over the spatial dimensions (i.e., predicted focus point locations (x,y)).

Figure 10:
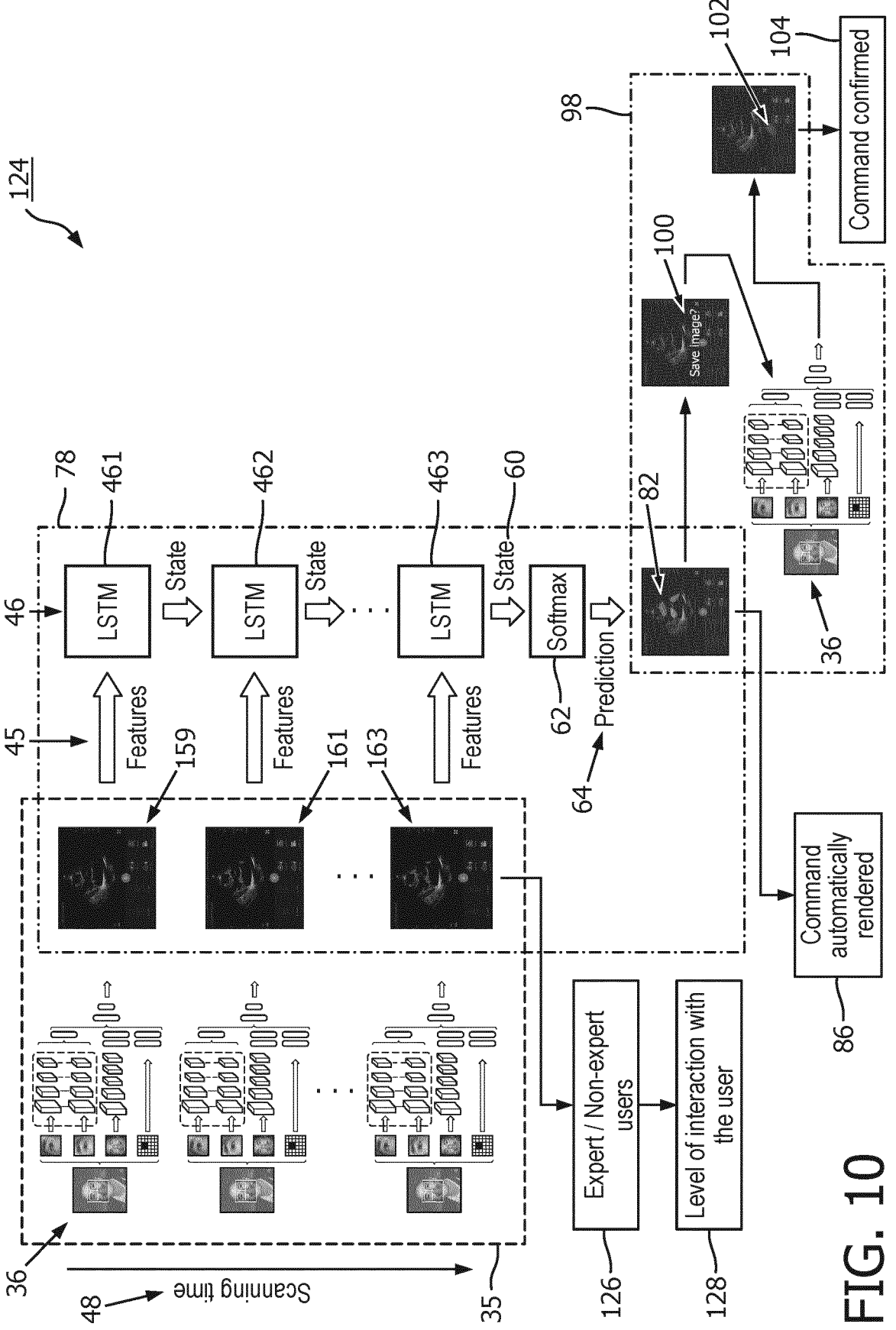
FIG. 10 is an overview flow-diagram view of different aspects of the method and ultrasound portable system according to various embodiments of the present disclosure.

Turning now to FIG. 10, there is shown an overview flow-diagram view 124 of different aspects of the method and ultrasound portable system according to various embodiments of the present disclosure. FIG. 10 illustrates a workflow and ensemble of those embodiments as previously described herein. One embodiment is represented by the flow-diagram view 35 of deep learning-based real-time eye-gaze tracking framework 36, for example, as discussed herein with reference to FIG. 5. Another embodiment is represented by the flow-diagram view 78 of predicted focus point locations and retrieval of complete eye movements per path for generating attention maps and predicted actions to command the ultrasound portable system 10, for example, as discussed herein with reference to FIG. 6. Yet another embodiment is represented by the flow diagram view 98 of eye-gaze tracking to confirm a command on the ultrasound portable system 10, for example, as discussed herein with reference to FIG. 7. Additional embodiments can include estimating a user's level of experience, whether an expert user or a novice (non-expert) user as indicated via reference numeral 126. Still further, a level of interaction with the device operator can be determined based on the estimate of the user's level of experience, as indicated via reference numeral 128. That is, the level of interaction between the user or device operator 12 and the smart device 14 is influenced based on the estimated level of user experience, as discussed previously herein.

To guarantee a scalability of the deep learning-based models discussed herein, the gaze and eye tracking from expert users is used for training. Furthermore, in order to have a robust eye tracking technique, a large variability of data is used in training of the deep learning-based models. Moreover, training with the large variability of data advantageously allows the ultrasound portable system and method of the present disclosure to be a calibration-free system and method during actual use.

Although only a few exemplary embodiments have been described in detail above, those skilled in the art will readily appreciate that many modifications are possible in the exemplary embodiments without materially departing from the novel teachings and advantages of the embodiments of the present disclosure. For example, an aspect of the embodiments of the present disclosure is to utilize eye tracking on ultrasound ultra-mobile platforms (e.g., Philips Lumify™). However, the embodiments may also be advantageous to ultrasound system devices that are other than portable devices. For instance, the embodiments of the present disclosure may also be applied to non-portable devices (e.g., EPIQ7™) to assist users during ultrasound scanning protocols, especially in ultrasound guided intervention procedures. In that instance, some adjustments may be needed, whereby the non-portable ultrasound system/device may not have a built-in camera and thus one or more external cameras need to be appropriately registered in order to calibrate and match the eye-gaze of the operator into the ultrasound image space (i.e., external cameras are calibrated in order to align user eye-gaze to monitors where ultrasound images are being displayed) to a display for the non-portable ultrasound system/device. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. A method for real-time eye-gaze tracking for an ultrasound portable system that comprises (i) a smart device having at least a display, (ii) a camera having a known spatial relationship relative to the display and (iii) an ultrasound probe coupled to the smart device, wherein the ultrasound portable system is for use by a device operator, the method comprising:

acquiring ultrasound images, via the smart device and the ultrasound probe over a period of time, wherein the period of time includes at least a portion of an ultrasound scan protocol and/or ultrasound exam;

presenting, via at least the display, at least one ultrasound image of the acquired ultrasound images in an image space portion of the display;

acquiring digital images, via the camera over the period of time, wherein an image content within a field of view of the camera includes at least the device operator's head pose, and left and right eyes within respective digital images;

determining eye-gaze focus point locations on the smart device within at least (i) the image space portion, (ii) a control space portion, or (iii) a combination of the image space and control space portions of the display relative to the camera, via an image processing framework, wherein the image processing framework is configured to track gaze and eye movement and takes as input the device operator's gaze and eye movement determined from the acquired digital images;

performing, via the smart device, one or more of a control function, a selection of a control function, and a function to aid in a selection of a diagnostic measurement according to the given ultrasound scan protocol and/or ultrasound exam, wherein the control function, selection of the control function, and the function to aid in the selection of the diagnostic measurement is based on at least one determined eye-gaze focus point location of the determined eye-gaze focus point locations; and generating, via the smart device, at least one attention map based on an accumulation of determined eye-gaze focus point locations for a given duration of time of an ultrasound acquisition, ultrasound scan protocol and/or ultrasound exam.

2. The method of claim 1, wherein the image processing framework comprises a deep learning framework that includes at least one or more Convolutional Neural Networks (CNNs), long-short term memory (LSTM) networks and/or recurrent neural networks (RRN), and/or a cascade of the at least one or more Convolutional Neural Networks (CNNs), long-short term memory (LSTM) networks and/or recurrent neural networks (RRN).

3. The method of claim 1, wherein the accumulation of determined eye-gaze focus point locations further defines a path that comprises a sequence of the determined eye-gaze focus point locations accumulated over time, wherein the path is identified with an action associated with a corresponding portion of the ultrasound scan protocol and/or ultrasound exam.

4. The method of claim 1, wherein the accumulation of determined eye-gaze focus point locations further defines a path that comprises a sequence of the determined eye-gaze focus point locations accumulated over time corresponding to contour points in an ultrasound image having a desired sharpness of contours, and wherein the action comprises freezing the at least one ultrasound image being displayed in the image space portion of the display.

5. The method of claim 2, further comprising:

comparing at least one generated attention map to one or more command attention maps stored in memory, each command attention map being based on a given track/path of the eyes for a given command of the ultrasound scan protocol and/or ultrasound exam; and executing, via the smart device, the given command, based on the comparison between the at least one generated attention map and the one or more command attention maps.

6. The method of claim 5, wherein the given command of a first command attention map of the one or more command attention maps comprises a command to automatically save the at least one ultrasound image being presented in the image space portion of the display.

7. The method of claim 5, wherein the given command of a second command attention map of the one or more command attention maps comprises one or more of (i) a command to automatically change an imaging modality of the ultrasound portable device from a first imaging modality to a second imaging modality, different from the first imaging modality, and (ii) a command to automatically select at least one ultrasound image from a cine-loop of multiple ultrasound images being displayed on the image space portion of the display.

8. The method of claim 5, the method further comprising:

outputting, via the smart device, at least one of a visual, audible, and/or tactile inquiry seeking confirmation for the smart device to execute the given command; and executing, via the smart device, the given command in response to receiving confirmation obtained via one or more determined eye-gaze focus point locations on the smart device within at least one of the image space portion or the control space portion of the display, via the deep learning framework.

9. The method of claim 8, wherein the inquiry seeking confirmation comprises an overlay message on the display.

10. The method of claim 5, further comprising:

determining, via the smart device, an experience level of the device operator, wherein the experience level comprises an indicator of whether the device operator is an expert or a non-expert device operator, based on one or more determined eye-gaze focus point locations on the smart device within at least one of the image space portion or the control space portion of the display, via the deep learning framework; and performing at least the portion of the ultrasound scan protocol and/or ultrasound exam with assistance based on the determined experience level, wherein the assistance includes (i) activating at least an inquiry seeking confirmation for the smart device to execute a given command in response to the determined experience level being a non-expert device operator, and (ii) deactivating the inquiry seeking confirmation in response the determined experience level being an expert device operator.

11. The method of claim 2, further comprising:

inputting, via the smart device, an experience level of the device operator, wherein the experience level comprises a grading indicator of which category, or class, the device operator belongs in, wherein the categories or classes include at least resident, novice, and experienced user; and providing, via the smart device, an additional input to the deep learning framework for gaze prediction that describes the experience of the device operator for improving a prediction accuracy of the deep learning framework.

12. The method of claim 1, wherein the camera comprises both a front-facing camera and a rear-facing camera, each having a respective fixed spatial relationship to the display, wherein the front-facing camera comprises the camera for acquiring digital images of the device operator, the method further comprising:

acquiring rear-facing digital images, via the rear-facing camera, over the period of time, of at least the ultrasound probe within a field of view of the rear-facing camera, wherein a content of the rear-facing digital images includes at least a pose of the device operator's hand, or a pose of the ultrasound probe, within respective rear-facing digital images; and augmenting the image space portion with one or more augmented reality (AR) marker based on one or more determined eye-gaze focus point location on the smart device.

13. The method of claim 12, further comprising:

presenting, via at least the display, at least one rear-facing digital image of the acquired rear-facing digital images, wherein the at least one rear-facing digital image is presented in the image space portion of the display, wherein determining eye-gaze focus point locations on the smart device within at least one of the image space portion or the control space portion of the display further includes tracking gaze and eye movement with respect to the at least one rear-facing digital image being presented and taking as input the device operator's gaze and eye movement determined from the digital images acquired via the front-facing camera.

14. The method of claim 1, further comprising:

calibrating, via the smart device, a gaze tracking algorithm of a deep learning framework, wherein calibrating includes:

starting the gaze tracking algorithm;

receiving, via the display, a tapping input at a defined eye-gaze focus point location on the display chosen by the device operator;

calculating an offset $(o_x, o_y)$ between (i) an estimated eye-gaze focus point location determined via the gaze tracking algorithm and (ii) the defined eye-gaze focus point location on the display;

repeating the steps of receiving and calculating for a plurality of additional defined eye-gaze focus point locations and calculated offsets, until one or more system requirements are met;

calculating an average offset $(\hat{o}_x, \hat{o}_y)$ between estimated and defined eye-gaze focus point locations; and using the average offset during subsequent use of the gaze tracking algorithm of the deep learning framework.

15. An ultrasound portable system with real-time eye-gaze tracking for use by a device operator, comprising:

a smart device having at least a display;

a camera having a fixed spatial relationship to the display, wherein the camera is communicatively coupled to the smart device; and an ultrasound probe communicatively coupled to the smart device; wherein the smart device is configured to:

acquire ultrasound images, via the ultrasound probe over a period of time, wherein the period of time includes at least a portion of an ultrasound scan protocol and/or ultrasound exam;

present, via at least the display, at least one ultrasound image of the acquired ultrasound images in an image space portion of the display;

acquire digital images, via the camera over the period of time, wherein an image content within a field of view of the camera includes at least the device operator's head pose, and left and right eyes within respective digital images;

determine eye-gaze focus point locations on the smart device within at least (i) the image space portion, (ii) a control space portion, or (iii) a combination of the image space and control space portions of the display relative to the camera, via an image processing framework, wherein the image processing framework is configured to track gaze and eye movement and takes as input the device operator's gaze and eye movement determined from the acquired digital images;

perform one or more of a control function, a selection of a control function, and a function to aid in a selection of a diagnostic measurement according to the given ultrasound scan protocol and/or ultrasound exam, wherein the control function, the selection of the control function, and the function to aid in the diagnostic measurement is based on at least one determined eye-gaze focus point location of the determined eye-gaze focus point locations; and generate, via the smart device, at least one attention map based on an accumulation of determined eye-gaze focus point locations for a given duration of time of an ultrasound acquisition, ultrasound scan protocol and/or ultrasound exam.

16. The system of claim 15, wherein the image processing framework comprises a deep learning framework that includes at least one or more Convolutional Neural Networks (CNNs), long-short term memory (LSTM) networks and/or recurrent neural networks (RRN), and/or a cascade of the at least one or more Convolutional Neural Networks (CNNs), long-short term memory (LSTM) networks and/or recurrent neural networks (RRN).

17. The system of claim 15, wherein the smart device is further configured to:
    compare at least one generated attention map to one or more command attention maps stored in memory, each command attention map being based on a given track/path of the eyes for a given command of the ultrasound scan protocol and/or ultrasound exam; and
    execute the given command, based on the comparison between the at least one generated attention map and the one or more command attention maps.

18. The system of claim 17, wherein the smart device is further configured to:
    output at least one of a visual, audible, and tactile inquiry seeking confirmation for the smart device to execute the given command; and
    execute the given command in response to receiving confirmation obtained via one or more determined eye-gaze focus point locations on the smart device within at least one of the image space portion or the control space portion of the display, via a deep learning framework.

19. The system of claim 15, wherein the camera comprises both a front-facing camera and a rear-facing camera, each having a fixed spatial relationship to the display, wherein the front-facing camera comprises the camera for acquiring digital images of the device operator, and wherein the smart device is further configured to:
    acquire rear-facing digital images, via the rear-facing camera, over the period of time, of at least the ultrasound probe within a field of view of the rear-facing camera, wherein a content of the rear-facing digital images includes at least a pose of the device operator's hand, or a pose of the ultrasound probe, within respective rear-facing digital images; and
    augment the image space portion with one or more augmented reality (AR) marker based on one or more determined focus point location on the smart device.

20. The system of claim 19, wherein the smart device is further configured to:
    present, via at least the display, at least one rear-facing digital image of the acquired rear-facing digital images, wherein the at least one rear-facing digital image is presented in the image space portion of the display, wherein the determined eye-gaze focus point locations on the smart device within at least one of the image space portion or the control space portion of the display further include determined eye-gaze focus point locations via a deep learning framework, and wherein the deep learning framework is further configured to track gaze and eye movement with respect to the at least one rear-facing digital image being presented and takes as input the device operator's gaze and eye movement determined from the digital images acquired via the front-facing camera.

* * * * *